United States Patent
Bauduin et al.

(10) Patent No.: US 11,986,798 B2
(45) Date of Patent: May 21, 2024

(54) PERMEABLE SUPERABSORBENT AND PROCESS FOR PRODUCTION THEREOF

(71) Applicant: BASF SE, Ludwigshafen (DE)

(72) Inventors: Christophe Bauduin, Ludwigshafen (DE); Thomas Daniel, Ludwigshafen (DE)

(73) Assignee: BASF SE, Ludwigshafen (DE)

(*) Notice: Subject to any disclaimer, the term of this patent is extended or adjusted under 35 U.S.C. 154(b) by 861 days.

(21) Appl. No.: 17/043,764

(22) PCT Filed: Apr. 1, 2019

(86) PCT No.: PCT/EP2019/058165
§ 371 (c)(1),
(2) Date: Sep. 30, 2020

(87) PCT Pub. No.: WO2019/197194
PCT Pub. Date: Oct. 17, 2019

(65) Prior Publication Data
US 2021/0016247 A1    Jan. 21, 2021

(30) Foreign Application Priority Data
Apr. 10, 2018 (EP) .................................... 18166564

(51) Int. Cl.
| | |
|---|---|
| *B01J 20/26* | (2006.01) |
| *A61L 15/18* | (2006.01) |
| *A61L 15/24* | (2006.01) |
| *A61L 15/54* | (2006.01) |
| *A61L 15/60* | (2006.01) |
| *B01J 20/08* | (2006.01) |
| *B01J 20/30* | (2006.01) |
| *C08F 220/06* | (2006.01) |

(52) U.S. Cl.
CPC ............ *B01J 20/267* (2013.01); *A61L 15/18* (2013.01); *A61L 15/24* (2013.01); *A61L 15/54* (2013.01); *A61L 15/60* (2013.01); *B01J 20/08* (2013.01); *B01J 20/3021* (2013.01); *B01J 20/3085* (2013.01); *C08F 220/06* (2013.01); *C08F 2800/10* (2013.01); *C08F 2810/20* (2013.01)

(58) Field of Classification Search
CPC ...... B01J 20/267; B01J 20/08; B01J 20/3021; B01J 20/3085; A61L 15/18; A61L 15/24; A61L 15/54; A61L 15/60; C08F 220/06; C08F 2800/10; C08F 2810/20; C08F 265/06; C08K 2003/2227; C08K 3/22; C08J 3/243; C08J 3/245; C08J 3/075; C08L 33/02; C08L 101/14
See application file for complete search history.

(56) References Cited

U.S. PATENT DOCUMENTS

| | | | |
|---|---|---|---|
| 3,932,322 A | 1/1976 | Duchane | |
| 5,145,906 A | 9/1992 | Chambers et al. | |
| 5,684,106 A | 11/1997 | Johnson et al. | |
| 6,620,889 B1 | 9/2003 | Mertens et al. | |
| 7,795,345 B2 | 9/2010 | Smith et al. | |
| 2009/0275470 A1* | 11/2009 | Nagasawa | B01J 20/0244 502/402 |
| 2016/0235882 A1 | 8/2016 | Noh et al. | |
| 2021/0187479 A1* | 6/2021 | Hartnagel | B01J 20/3236 |

FOREIGN PATENT DOCUMENTS

| | | |
|---|---|---|
| EP | 0233067 A2 | 8/1987 |
| EP | 0780424 A1 | 6/1997 |
| EP | 1209186 A1 | 5/2002 |
| EP | 3112383 A1 | 1/2017 |
| JP | H09124879 A | 5/1997 |
| JP | 3121934 B2 | 1/2001 |
| WO | WO-98/48857 A1 | 11/1998 |
| WO | WO-99/55767 A1 | 11/1999 |
| WO | WO-01/68156 A1 | 9/2001 |
| WO | WO-01/74913 A1 | 10/2001 |
| WO | WO-03/049778 A1 | 6/2003 |
| WO | WO-2004/113452 A1 | 12/2004 |

(Continued)

OTHER PUBLICATIONS

"Modern Superabsorbent Polymer Technology", ed. Buchholz, et al., 1 Edition, 1997.

(Continued)

*Primary Examiner* — Andrew J. Oyer
(74) *Attorney, Agent, or Firm* — MARSHALL, GERSTEIN & BORUN LLP

(57) ABSTRACT

A highly permeable superabsorbent is prepared by a process comprising
polymerizing an aqueous monomer solution comprising
  a) at least one ethylenically unsaturated monomer which bears acid groups and is optionally at least partly in salt form,
  b) at least one crosslinker,
  c) at least one initiator,
  d) optionally one or more ethylenically unsaturated monomers copolymerizable with the monomers mentioned under a), and
  e) optionally one or more water-soluble polymers;
drying the resulting polymer,
optionally grinding the dried polymer and sieving the ground polymer,
optionally surface postcrosslinking the dried and optionally ground and sieved polymer,
wherein, after drying, grinding or sieving, and, if surface postcrosslinking is conducted, during or after this surface postcrosslinking, x-ray-amorphous aluminum hydroxide powder is added.

8 Claims, No Drawings

(56) References Cited

FOREIGN PATENT DOCUMENTS

| WO | WO-2005/108472 A1 | 11/2005 |
|---|---|---|
| WO | WO-2006/111402 A2 | 10/2006 |
| WO | WO-2007/074108 A1 | 7/2007 |
| WO | WO-2007/121941 A2 | 11/2007 |
| WO | WO-2009/080611 A2 | 7/2009 |
| WO | WO-2010/108875 A1 | 9/2010 |
| WO | WO-2012/045705 A1 | 4/2012 |
| WO | WO-2012/143215 A1 | 10/2012 |
| WO | WO-2013/72311 A1 | 5/2013 |
| WO | WO-2013/076031 A1 | 5/2013 |
| WO | WO-2013/156281 A1 | 10/2013 |
| WO | WO-2013/156330 A1 | 10/2013 |
| WO | WO-2014/167036 A1 | 10/2014 |
| WO | WO-2014/167040 A1 | 10/2014 |
| WO | WO-2014/168858 A1 | 10/2014 |
| WO | WO-2019/091848 A1 | 5/2019 |

OTHER PUBLICATIONS

International Application No. PCT/EP2019/058165, International Search Report, dated Jul. 5, 2019.

\* cited by examiner

PERMEABLE SUPERABSORBENT AND PROCESS FOR PRODUCTION THEREOF

CROSS-REFERENCE TO RELATED APPLICATIONS

This is the U.S. national phase of International Application No. PCT/EP2019/058165, filed Apr. 1, 2019, which claims the benefit of European Patent Application No. 18166564.7, filed on Apr. 10, 2018.

The present invention relates to a permeable superabsorbent, to a process for producing it and to its use and to hygiene articles comprising it.

Superabsorbents are known. For such materials, names such as "highly swellable polymer", "hydrogel" (often also used for the dry form), "hydrogel-forming polymer", "water-absorbing polymer", "absorbent gel-forming material", "swellable resin", "water-absorbing resin" or the like are also commonly used. These materials are crosslinked hydrophilic polymers, more particularly polymers formed from (co)polymerized hydrophilic monomers, graft (co) polymers of one or more hydrophilic monomers on a suitable graft base, crosslinked cellulose ethers or starch ethers, crosslinked carboxymethylcellulose, partly crosslinked polyalkylene oxide or natural products swellable in aqueous liquids, for example guar derivatives, the most common being water-absorbing polymers based on partly neutralized acrylic acid. The essential properties of superabsorbents are their abilities to absorb several times their own weight of aqueous liquids and not to release the liquid again even under a certain pressure. The superabsorbent, which is used in the form of a dry powder, is converted to a gel when it absorbs fluid, and correspondingly to a hydrogel when it absorbs water as usual. Crosslinking is essential for synthetic superabsorbents and is an important difference from customary straightforward thickeners, since it leads to the insolubility of the polymers in water. Soluble substances would be unusable as superabsorbents. By far the most important field of use of superabsorbents is the absorption of body fluids. Superabsorbents are used, for example, in diapers for infants, incontinence products for adults or feminine hygiene products. Other fields of use are, for example, as water-retaining agents in market gardening, as means of water storage for protection from fire, for fluid absorption in food packaging, or quite generally for absorbing moisture.

Superabsorbents are capable of absorbing several times their own weight of water and of retaining it under a certain pressure. In general, such a superabsorbent has a CRC ("centrifuge retention capacity", see below for test method) of at least 5 g/g, preferably at least 10 g/g and more preferably at least 15 g/g. A "superabsorbent" may also be a mixture of different individual superabsorbent substances or a mixture of components which exhibit superabsorbent properties only when they interact; it is not so much the physical composition as the superabsorbent properties that are important here.

Important features for a superabsorbent are not only its absorption capacity, but also the ability to retain fluid under pressure (retention, usually expressed as "Absorption under Load" ("AUL") or "Absorption against Pressure" ("AAP"), for test method see below) and the permeability, i.e. the ability to conduct fluid in the swollen state (usually expressed as "Saline Flow Conductivity" ("SFC") or as "Gel Bed Permeability" ("GBP"), for test method see below (although changes to the superabsorbent do not necessarily alter both its SFC and GBP values, or alter them to the same degree)). Swollen gel can hinder or prevent fluid conductivity to as yet unswollen superabsorbent ("gel blocking"). Good conductivity properties for fluids are possessed, for example, by hydrogels which have a high gel strength in the swollen state. Gels with only a low gel strength are deformable under an applied pressure (body pressure), block pores in the superabsorbent/cellulose fiber absorbent core and thus prevent fluid conductivity to as yet unswollen or incompletely swollen superabsorbent and fluid absorption by this as yet unswollen or incompletely swollen superabsorbent. An increased gel strength is generally achieved through a higher degree of crosslinking, but this reduces the absorption capacity of the product. An elegant method of increasing the gel strength is that of increasing the degree of crosslinking at the surface of the superabsorbent particles compared to the interior of the particles. To this end, superabsorbent particles which have usually been dried in a surface postcrosslinking step and have an average crosslinking density are subjected to additional crosslinking in a thin surface layer of the particles thereof. The surface postcrosslinking increases the crosslinking density in the shell of the superabsorbent particles, which raises the absorption under compressive stress to a higher level. While the absorption capacity in the surface layer of the superabsorbent particles falls, their core, as a result of the presence of mobile polymer chains, has an improved absorption capacity compared to the shell, such that the shell structure ensures improved permeability, without occurrence of gel blocking. It is likewise known that superabsorbents which are relatively highly crosslinked overall can be obtained, and that the degree of crosslinking in the interior of the particles can subsequently be reduced compared to an outer shell of the particles.

Processes for producing superabsorbents are also known. Superabsorbents based on acrylic acid, which are the most common on the market, are produced by free-radical polymerization of acrylic acid in the presence of a crosslinker (the "inner crosslinker"), the acrylic acid being neutralized to a certain degree before, after or partly before and partly after the polymerization, typically by adding alkali, usually an aqueous sodium hydroxide solution. The polymer gel thus obtained is comminuted (according to the polymerization reactor used, this can be done simultaneously with the polymerization) and dried. The dry powder thus obtained (the "base polymer") is typically postcrosslinked on the surface of the particles, by reacting it with further crosslinkers, for instance organic crosslinkers or polyvalent cations, for example aluminum (usually used in the form of aluminum sulfate) or both, in order to obtain a more highly crosslinked surface layer compared to the particle interior.

Fredric L. Buchholz and Andrew T. Graham (editors), in: "Modern Superabsorbent Polymer Technology", J. Wiley & Sons, New York, U.S.A./Wiley-VCH, Weinheim, Germany, 1997, ISBN 0-471-19411-5, give a comprehensive review of superabsorbents, the properties thereof and processes for producing superabsorbents.

Treating superabsorbents with aluminum compounds is known. For example, superabsorbents are powdered with inorganic fine particles in order to lower the tendency to caking and to increase the flowability of the powder or else its permeability. Usually, precipitated silicon dioxide is used for this purpose, but U.S. Pat. No. 7,795,345 B2, 3,932,322 or WO 2013/076031 A1 also disclose the addition of pyrogenic silicon or aluminum oxides to superabsorbents. According to the teaching of WO 01/68 156 A1, aluminosilicates, for example zeolite, are added to superabsorbents in order to increase permeability and bind unpleasant odors. WO 2007/74 108 A1 teaches coating superabsorbents with non-reactive and non-film-forming compounds, for example with water-insoluble salts. Hydrated aluminum oxide is mentioned among a number of such salts. WO 2007/121 941 A2 discloses similar superabsorbents coated with inorganic powders, where the powders may also be provided with a binder. Aluminium hydroxide is mentioned among a number of inorganic powders.

Also known, although extremely rarely if ever practiced, is the use of polyvalent cations such aluminum as internal crosslinker of superabsorbents. By contrast, the addition of polyvalent cations to superabsorbents in the course of surface postcrosslinking with surface postcrosslinkers which form covalent bonds between the polymer chains is customary.

WO 99/55 767 A1 discloses superabsorbents to which, before, during or after the polymerization, aluminates of the formula $M_n[H_{2n+2}AlnO_{3n+1}]$ with M=K or Na and n=an integer from 1 to 10 are added. WO 98/48 857 A1 describes superabsorbents which are crosslinked with Al, Fe, Zr, Mg or Zn cations and then mixed with a liquid such as water, mineral oil or polyols. WO 01/74 913 A1 relates to the regeneration of superabsorbents, specifically to the increase in a permeability reduced by attrition, by addition of a solution of an at least trivalent cation, typically of an aqueous aluminum sulfate solution. U.S. Pat. No. 6,620,889 B1 discloses superabsorbents which are surface postcrosslinked with a combination of a polyol and a salt of a polyvalent metal in aqueous solution. The anion of the salt may be chloride, bromide, sulfate, carbonate, nitrate, phosphate, acetate or lactate. The use of aluminum sulfate is preferred.

According to the teaching of WO 2006/111 402 A2, a base polymer is treated with a permeability improver selected from silicon-oxygen compounds, salts of polyvalent, especially trivalent, cations or mixtures thereof. The salt of a trivalent cation is preferably an aluminum salt, which is selected from a group of salts including aluminum lactate, oxalate, citrate, glyoxylate, succinate, tartrate and other organic and inorganic aluminum salts. WO 2005/108 472 A1 discloses a process which comprises the treatment of a base polymer with a water-soluble salt of a polyvalent metal and an organic acid or salt thereof. The salt of a polyvalent metal is preferably aluminum sulfate. The organic acid or salt thereof is selected from a group of acids including citric acid, glyoxylic acid, glutaric acid, succinic acid, tartaric acid, lactic acid and the alkali metal or ammonium salts of these acids.

WO 2004/113 452 A1 describes superabsorbents which are treated with concentrated solutions of polyvalent metal salts, especially sodium aluminate. WO 2013/156 281 A1 teaches the treatment of superabsorbents with aluminum glycinate. WO 2010/108 875 A1, WO 2012/045 705 A1 and WO 2013/156 330 A1 teach the treatment of superabsorbents with basic aluminum salts such as basic aluminum acetate or aluminum lactate.

WO 2009/080 611 A2 discloses the treatment of superabsorbents with mixtures of aluminum salts, one of which comprises a chelating anion, for example dicarboxylates or hydroxycarboxylates, particular preference being given to lactate, and the other a weakly complexing anion, for example chloride, nitrate, sulfate, hydrogensulfate, carbonate, hydrogencarbonate, nitrate, phosphate, hydrogenphosphate, dihydrogenphosphate or carboxylate, particular preference being given to sulfate. Prior application 17 200 963.1 at the European Patent Office teaches a superabsorbent complexed with aluminum ions, where the aluminum ions are applied in the form of an aqueous solution comprising aluminum ions, which has the feature that it comprises aluminum ions in a proportion within the range of 0.5%-15% by weight (optionally converted to $Al^{3+}$), based on the total mass of the solution, and further comprises anions of lactic acid (lactate ions) and phosphoric acid (phosphate ions), where the molar proportion of the lactate ions is within the range of 0.01-2.99 times the molar amount of $Al^{3+}$ and the molar proportion of the phosphate ions is within the range of 0.01-2.99 times the molar amount of $Al^{3+}$. These solutions are prepared by adding acid to amorphous aluminum hydroxide.

EP 233 067 A2 discloses the surface postcrosslinking of superabsorbents with aluminum salts that can react with the superabsorbent in the presence of polyol and water. Among a number of aluminum salts, aluminum hydroxide is also mentioned. The use of freshly precipitated aluminum hydroxide sol or gel is recommended. According to the teaching of U.S. Pat. No. 5,145,906, undried polymerized gel is treated with a surface postcrosslinker; the surface postcrosslinking reaction takes place in the course of heating for drying or during the drying. Aluminum hydroxide is one of the possible surface postcrosslinkers mentioned. JP 09/124 879 A likewise mentions, among a number of compounds, aluminum hydroxide for this purpose, but this, like the other water-soluble compounds mentioned, is to be applied as a solution. EP 780 424 A1 mentions the hydroxides and chlorides of a number of metals, including aluminum, as surface postcrosslinkers. U.S. Pat. No. 5,684,106 mentions aluminum sulfate, sodium aluminate or other polyvalent metal compounds for this purpose. JP 3 121 934 B teaches, for this purpose, the use of polyaluminum hydroxides of the formula $[Al(OH)_3]_n \cdot AlCl_3$ with n=10-21).

WO 03/049 778 A1 teaches, in the case of superabsorbents postcrosslinked with either covalent surface postcrosslinkers or polyvalent metal ions, after a first absorption of liquid, redissolving the postcrosslinking with metal ions, for example complexing agents, in order to obtain further absorption capacity thereby. Aluminum hydroxide is mentioned among a number of possible polyvalent metal salts as postcrosslinkers.

According to the teaching of WO 2012/143 215 A1, a solution of a neutralized polyvalent metal salt, preferably of an aluminum salt which is formed from an aluminum compound and an organic acid with a chelate-forming anion, and wherein the solution is neutralized to a pH between 5 and 9 with acid or base, is added to the superabsorbent. The aluminum compound that has thus been reacted with an acid having a chelate-forming anion may also be aluminum hydroxide. The organic chelate-forming anions mentioned form a water-soluble complex with the metal ion. WO 2013/72 311 A1 teaches surface postcrosslinking using a complex of a metal salt, for instance aluminum hydroxide, and a 2-hydroxycarboxamide.

WO 2014/167 036 A1, WO 2014/167 040 and WO 2014/168 858 A1 disclose, like EP 233 067 A2 already cited above, the application of freshly precipitated aluminum hydroxide sol in the surface postcrosslinking.

US 2016/0 235 882 A1 teaches, prior to application of a solution of a covalent postcrosslinker, mixing of aluminum hydroxide powder into the superabsorbent base polymer. The mixing-in is preferably effected in dry form since there is a rise in the tendency to caking on application of suspensions.

There still remains the problem of finding different or even improved superabsorbents, in particular permeable superabsorbents, and very substantially simplified or improved processes for production thereof. There should be at least only insignificant, if any, impairment of the use properties of the superabsorbent, especially its absorption capacity for liquid, including under pressure, and its swelling kinetics, quantified as volumetric absorption under pressure "VAUL". Further objects of the invention are uses of this superabsorbent, such as hygiene products comprising this superabsorbent and processes for production thereof.

The object was achieved by a process for producing a superabsorbent, comprising polymerizing an aqueous monomer solution comprising a) at least one ethylenically unsaturated monomer which bears acid groups and is optionally at least partly in salt form,
 b) at least one crosslinker,
 c) at least one initiator,
 d) optionally one or more ethylenically unsaturated monomers copolymerizable with the monomers mentioned under a), and
 e) optionally one or more water-soluble polymers, drying the resulting polymer,
optionally grinding the dried polymer and sieving the ground polymer,
optionally surface postcrosslinking of the dried and optionally ground and sieved polymer,
wherein, after drying, grinding or sieving, and, if surface postcrosslinking is conducted, during or after this surface postcrosslinking, x-ray-amorphous aluminum hydroxide powder is added.

The superabsorbents of the invention are obtainable by the process of the invention and are preferably produced by the process of the invention. They show surprisingly good permeability, without any significant impairment in their other use properties such as CRC or AUL.

Articles for absorption of fluids have additionally been found, especially hygiene articles for absorption of fluid excretions or fluid components of excretions, which comprise the superabsorbent of the invention. Processes for production of such articles for absorption of fluids have also been found, the production of these articles involving addition of the superabsorbent of the invention thereto.

In the production of the superabsorbent of the invention in the process of the invention, x-ray-amorphous aluminum hydroxide is added.

The addition of polyvalent metal salts to superabsorbents has long been known. Usually, aluminum salts are added. The addition is typically effected in the course of surface postcrosslinking with a covalent surface postcrosslinking, i.e. a compound that can form covalent bonds with functional groups at the surface of the superabsorbent particles, typically the acid groups of the customary acrylic acid-based superabsorbents. Ultimately, the addition of polyvalent metal salts also leads to crosslinking sites at the surface of the superabsorbent particles, but by ionic bonding. The treatment of superabsorbents with polyvalent metal ions in the course of surface postcrosslinking is often referred to as "complexation". "Complexation" is thus, strictly speaking, solely a specific term for the special case of surface postcrosslinking in which polyvalent metal ions produce ionic bonds between several polar groups at the surface of the superabsorbent particles, and complexation is often also discussed under "surface postcrosslinking". In the context of this invention, "complexation" is understood to mean surface postcrosslinking with polyvalent metal ions, especially aluminum, in order to delimit it from surface postcrosslinking with postcrosslinkers which form covalent bonds with polar groups at the surface of the superabsorbent particles.

In complexation, the added metal salt is reacted with the superabsorbent. The x-ray-amorphous aluminum hydroxide added here to the superabsorbent in accordance with the invention is therefore not or at least not completely conserved as such in the superabsorbent. What is therefore essential is that the superabsorbent of the invention has been treated with x-ray-amorphous aluminum hydroxide—or in other words that it has been added thereto. It may but need not still comprise added x-ray-amorphous aluminum hydroxide as such.

Aluminum hydroxide is understood here to mean aluminum trihydroxide. The nomenclature is not treated uniformly in the literature. More particularly, aluminum hydroxide is often also counted among the aluminum hydroxide hydrates or else referred to as hydrated aluminum oxide. Aluminum hydroxide is precipitated in a known manner from aluminum salt solutions by addition of base or from aluminate solutions by addition of acid, in each case to the neutral pH region. For preparation of amorphous aluminum hydroxide, precipitation has to be effected rapidly since, in the case of slow precipitation, crystalline gamma-$Al(OH)_3$ ("hydrargillite" or "gibbsite") forms from aluminate solutions or alpha-$Al(OH)_3$ ("bayerite") from aluminum salt solutions. Bayerite is gradually converted to hydrargillite over time. These hydroxides can condense slowly to form the aluminum hydroxide hydrates of the formula $Al(O)OH$ (diaspore or boehmite), which are occasionally also referred to as "hydroxides". In the production of x-ray-amorphous aluminum trihydroxide, therefore, rather than seeding with crystalline aluminum hydroxide as in the Bayer process for preparation of aluminum hydroxide hydrates, there is rapid precipitation and rapid drying. Preference is given to drying freshly precipitated aluminum hydroxide gel by means of spray drying. The chemistry and preparation of aluminum hydroxide, oxide hydrate and oxide are well-known; see, for example, Holleman/Wiberg, Lehrbuch der Anorganischen Chemie [Inorganic Chemistry], Walter de Gruyter & Co., Berlin, 103rd edition 2016, ISBN 978-3-11-051854-2, section 2.4 "Sauerstoffverbindungen des Aluminiums" [Oxygen Compounds of Aluminum], or Ullmann's Encyclopedia of Industrial Chemistry, under "Aluminum Oxide", Wiley-VCH Verlag Gmbh & Co. KGaA, Weinheim 2012, DOI 10.1002/14356007.a01_557. Some structural differences between amorphous and crystalline aluminum hydroxide at the atomic/molecular level are elucidated by T. Isobe et al., J. Colloid and Interface Science 261 (2003) 320-324, which incidentally also mentions further known methods of production of amorphous aluminum hydroxide by way of introduction. X-ray-amorphous aluminum hydroxide in powder form is also commercially available, for example as "aluminum hydroxide dried gel", catalog number 511066100, from Dr. Paul Lohmann GmbH KG, Hauptstrasse 2, 31860 Emmerthal, Germany.

Aluminum hydroxide is x-ray-amorphous when it does not show any signals ("lines") in an x-ray powder diffractogram. Crystalline substances diffract electromagnetic radiation having a wavelength in the order of magnitude of the interatomic distances—x-radiation is typically used—such that a diffraction pattern of the radiation can be measured. When single crystals are sufficiently large, they result in diffraction patterns in the form of dots, in which the crystal structure including the position of the atoms in the crystal lattice can be calculated from the position and intensity of the dots. It is possible to measure a diffractogram on a powder of a crystalline substance that shows maxima of the scattered x-radiation as a function of the deflection angle as signals ("lines"), where the half-height width of the maxima correlates with the size of the crystals in the powder. All of this is well-known; see, for example, Ullmann's Encyclopedia of Industrial Chemistry, under "Structure Analysis by Diffraction", Wiley-VCH Verlag GmbH & Co. KGaA, Weinheim 2012, DOI 10.1002/14356007.b05_341. The method is established, and instruments for measurement of powder diffractograms are commercially available.

Accordingly, powders show no signals in the x-ray diffractogram when they have no crystal structure, the atoms or molecules are thus in entirely or largely unordered form, or the crystals are so small that the number of unit cells in the crystal that are arranged to form the crystal is insufficient for focused diffraction of radiation and the half-height width of the maxima in the diffractogram becomes so great that they disappear in the baseline and it is possible to measure only diffuse radiation. What is crucial here is the size of the crystals in the powder, not the particle size of the powder. In one powder particle, it is possible for numerous smaller crystals ("primary crystals" or "primary crystallites") to be agglomerated or bonded in some other way. For the x-ray-amorphous aluminum hydroxide used here in accordance with the invention, that the primary crystallites present therein—if any are present—have a size of not more than 2 nm.

The x-ray-amorphous aluminum hydroxide can be used in a mixture with crystalline aluminum hydroxide. In this case, lines attributable to the crystalline component may occur in the diffractogram of the mixture. The proportion of crystalline aluminum hydroxide can also be determined, for example, by calibrating a powder diffractogram, by adding a known amount of crystalline aluminum hydroxide to a comparative sample of the powder and expressing the increase in the total area of all lines in the diffractogram that results therefrom in relation to the area of all lines in the diffractogram of the actual sample. All of this is known, and is no different in the calibration of chromatographs for instance.

In general, the total aluminum hydroxide added has a proportion of at least 50% by weight of x-ray-amorphous aluminum hydroxide, preferably of at least 70% by weight and more preferably of at least 90% by weight. What is desirable is pure x-ray-amorphous aluminum hydroxide without crystalline components that occur in an x-ray diffractogram, or at least aluminum hydroxide which, apart from unavoidable small crystalline fractions (as occur, for instance, in the course of aging), consists solely of x-ray-amorphous aluminum hydroxide.

According to the invention, the x-ray-amorphous aluminum hydroxide is added generally in an amount of at least 0.01% by weight, preferably at least 0.1% by weight and more preferably of at least 0.2% by weight, even more preferably of at least 0.3% by weight, and generally of at most 2% by weight, preferably at most 1.5% by weight and more preferably of at most 1% by weight, even more preferably at most 0.7% by weight, based in each case on the superabsorbent prior to the addition.

According to the invention, the x-ray-amorphous aluminum hydroxide is added as powder after drying, grinding or sieving, and, if surface postcrosslinking is conducted, during or after this surface postcrosslinking.

In the process of the invention, the x-ray-amorphous aluminum hydroxide is accordingly mixed dry into the superabsorbent powder after drying thereof, and, if a sieve fraction of the superabsorbent is obtained after drying, into this sieving step. This can be effected by any known mixing apparatus and process and is preferably conducted in mixers with moving mixing tools, for example screw mixers, disk mixers, paddle mixers or shovel mixers, or mixers with other mixing tools. Suitable mixers are obtainable, for example, as Pflugschar® (plowshare) mixers from Gebr. Lödige Maschinenbau GmbH, Elsener-Strasse 7-9, 33102 Paderborn, Germany.

Preferably, after the x-ray-amorphous aluminum hydroxide has been mixed in, the superabsorbent thus produced is moistened, i.e. its water content is increased. For this purpose, in a dedicated apparatus or conveniently in the same mixer, water is added, for instance by spray application via a nozzle, likewise in the manner described below for the spray application of a postcrosslinker solution. In general, in that case, water is added to the superabsorbent in an amount of at least 0.1% by weight, preferably of at least 0.5% by weight and more preferably at least 1% by weight, and generally at most 10% by weight, preferably at most 7% by weight and more preferably at most 5% by weight, based in each case on the superabsorbent prior to the addition.

If the superabsorbent is not warm or hot (for instance after a preceding drying operation) at the time of addition of water, it may be advantageous to add heated water in this remoisturizing operation. In general, water is added at a temperature of at least 5° C., preferably at least 20° C. and more preferably at least 25° C., for example water at a temperature of 30° C., 40° C., 50° C., 60° C., 70° C., 80° C. or 90° C. It is also possible to use steam.

The addition of x-ray-amorphous aluminum hydroxide and optionally that of water can be effected before, during or after surface postcrosslinking. If the surface postcrosslinker solution to be applied comprises water, it is conveniently possible to conduct the addition of x-ray-amorphous aluminum hydroxide beforehand and replace addition of the surface postcrosslinker solution the optional addition of water after the addition of x-ray-amorphous aluminum hydroxide.

The total amount of x-ray-amorphous aluminum hydroxide to be added can also be divided between multiple addition sites or junctures. Preference is given to addition at one site and at one juncture.

For the rest, the process of the invention for production of superabsorbents is known. It is a process for aqueous solution polymerization of a monomer mixture comprising the following:
 a) at least one ethylenically unsaturated monomer which bears at least one acid group and is optionally at least partly in salt form,
 b) at least one crosslinker,
 c) at least one initiator,
 d) optionally one or more ethylenically unsaturated monomers copolymerizable with the monomers mentioned under a), and
 e) optionally one or more water-soluble polymers.

The monomers a) are preferably water-soluble, i.e. their solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids or salts thereof, such as acrylic acid, methacrylic acid, maleic acid or salts thereof, maleic anhydride and itaconic acid or salts thereof. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, an acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomer solution comprises preferably at most 250 ppm by weight, preferably at most 130 ppm by weight, more preferably at most 70 ppm by weight and preferably at least 10 ppm by weight, more preferably at least 30 ppm by weight, especially around 50 ppm by weight, of hydroquinone monoether, based in each case on the unneutralized monomer a); neutralized monomer a), i.e. a salt of the monomer a), is considered for arithmetic purposes to be unneutralized monomer. For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 530 438 A1, di- and triacrylates, as described in EP 547 847 A1, EP 559 476 A1, EP 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/32962 A2.

Preferred crosslinkers b) are pentaerythrityl triallyl ether, tetraallyloxyethane, methylenebismethacrylamide, 15- to 20-tuply ethoxylated trimethylolpropane triacrylate, 15-20-tuply ethoxylated glyceryl triacrylate, polyethylene glycol diacrylate having between 4 and 45 —$CH_2CH_2O$ units in the molecule chain, trimethylolpropane triacrylate and triallylamine.

Very particularly preferred crosslinkers b) are the polyethoxylated and/or propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05% to 1.5% by weight, more preferably 0.1% to 1% by weight, most preferably 0.3% to 0.6% by weight, based in each case on monomer a). With rising crosslinker content, there is a fall in the centrifuge retention capacity (CRC) and a rise in the absorption under load (AUL).

The initiators c) used may be all compounds which generate free radicals under the polymerization conditions, for example thermal initiators, redox initiators and/or photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. However, the reducing component used is preferably also a sulfonic acid derivative, for example a mixture of the sodium salt of 2-hydroxy-2-sulfinatoacetic acid, the disodium salt of 2-hydroxy-2-sulfonatoacetic acid and sodium bisulfite, obtainable, for example, from L. Brüggemann KG (Salzstrasse 131, 74076 Heilbronn, Germany, www.brueggemann.com) under the BRÜGGOLIT® FF6M or BRÜGGOLIT® FF7, or alternatively BRUGGOLITE® FF6M or BRUGGOLITE® FF7 names, or the disodium salt of 2-hydroxy-2-sulfonatoacetic acid, obtainable, for example, from L. Brüggemann KG under the BLANCOLEN® HP name. The initiators are, incidentally, used in customary amounts. The customary amount of the reducing component of a redox initiator is generally at least 0.00001% by weight, preferably at least 0.0001% by weight and more preferably at least 0.001% by weight, and generally at most 0.2% by weight and preferably at most 0.1% by weight, based in each case on the amount of monomers a) and d). If, however, the sole reducing component used in the redox initiator is sulfonic acid derivative, the added amount thereof is generally at least 0.001% by weight, preferably at least 0.01% by weight and more preferably at least 0.03% by weight, and generally at most 1.0% by weight, preferably at most 0.3% by weight and more preferably at most 0.2% by weight, based in each case on the amount of monomers a) and d). The customary amount of the oxidizing component of a redox initiator is generally 0.0001% by weight and more preferably at least 0.001% by weight, and generally at most 2% by weight and preferably at most 1.0% by weight, based in each case on the amount of monomers a) and d).

The customary amount of the thermal initiators is generally 0.01% by weight and more preferably at least 0.1% by weight, and generally at most 2% by weight and preferably at most 1.0% by weight, based in each case on the amount of monomers a) and d). The customary amount of the photoinitiators is generally 0.001% by weight and more preferably at least 0.01% by weight, and generally at most 1.0% by weight and preferably at most 0.2% by weight, based in each case on the amount of monomers a) and d).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate, maleic acid or salts thereof and maleic anhydride.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40% to 75% by weight, more preferably from 45% to 70% by weight and most preferably from 50% to 65% by weight. It is also possible to use monomer suspensions, i.e. oversaturated monomer solutions. As the water content rises, the energy expenditure in the subsequent drying rises and, as the water content falls, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

The monomer mixture may comprise further components. Examples of further components used in such monomer mixtures are, for instance, chelating agents in order to keep metal ions in solution, or inorganic powders in order to increase the stiffness of the superabsorbent in the swollen state, or recycled undersize from a later grinding operation. It is possible here to use all known additions to the monomer mixture. Even though only "solution" is discussed here in connection with the monomer mixture, this also means the polymerization of a suspension, for instance when insoluble constituents are added to the monomer mixture.

The acid groups of the polymer gels resulting from the polymerization have typically been partly neutralized. Neutralization is preferably carried out at the monomer stage; in other words, salts of the monomers bearing acid groups or, to be precise, a mixture of monomers bearing acid groups and salts of the monomers bearing acid groups ("partly neutralized acid") are used as component a) in the polymerization. This is typically accomplished by mixing the neutralizing agent as an aqueous solution or preferably also as a solid into the monomer mixture intended for polymerization or preferably into the monomer bearing acid groups or a solution thereof. The degree of neutralization is preferably from 25 to 95 mol %, more preferably from 50 to 80 mol % and most preferably from 65 to 72 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably 10 to 30 mol % and more preferably 15 to 25 mol % of the acid groups before the polymerization by adding a portion of the neutralizing agent directly to the monomer solution and setting the desired final degree of neutralization only after the polymerization, at the polymer gel stage. When the polymer gel is at least partly neutralized after the polymerization, the polymer gel is preferably comminuted mechanically, for example by means of an extruder, in which case the neutralizing agent can be sprayed, sprinkled or poured on and then carefully mixed in. For this purpose, the gel material obtained can be extruded several times more for homogenization.

However, preference is given to performing the neutralization at the monomer stage. In other words, in a very particularly preferred embodiment, the monomer a) used is a mixture of 25 to 95 mol %, more preferably from 50 to 80 mol % and most preferably from 65 to 75 mol % of salt of the monomer bearing acid groups, and the remainder to 100 mol % of monomer bearing acid groups. This mixture is, for example, a mixture of sodium acrylate and acrylic acid or a mixture of potassium acrylate and acrylic acid.

In a preferred embodiment, the neutralizing agent used for the neutralization is one whose iron content is generally below 10 ppm by weight, preferably below 2 ppm by weight and more preferably below 1 ppm by weight. Likewise desired is a low content of chloride and anions of oxygen acids of chlorine. A suitable neutralizing agent is, for example, the 50% by weight sodium hydroxide solution or potassium hydroxide solution which is typically traded as "membrane grade"; even more pure and likewise suitable, but also more expensive, is the 50% by weight sodium hydroxide solution or potassium hydroxide solution typically traded as "amalgam grade" or "mercury process".

Processes for production of superabsorbents from monomer mixtures, such as those described by way of example above, are known in principle. Suitable polymerization reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/38402 A1. Polymerization on a belt is described, for example, in EP 955 086 A2, DE 38 25 366 A1 and U.S. Pat. No. 6,241,928. Polymerization in a belt reactor forms, like the likewise known polymerization in batchwise operation or in a tubular reactor, as described, for example, in EP 445 619 A2 and DE 19 846 413 A1, a polymer gel which has to be comminuted in a further process step, for example in a meat grinder, extruder or kneader. It is also possible to produce spherical or differently shaped superabsorbent particles by suspension or emulsion polymerization, as described, for example, in EP 457 660 A1, or by spray or droplet polymerization processes, as described, for example, in EP 348 180 A1, EP 816 383 A1, WO 96/404 27 A1, U.S. Pat. No. 4,020,256, US 2002/0 193 546 A1, DE 35 19 013 A1, DE 10 2005 044 035 A1, WO 2007/093531 A1, WO 2008/086 976 A1 or WO 2009/027 356 A1. Likewise known are processes in which the monomer mixture is applied to a substrate, for example a nonwoven web, and polymerized, as described, for instance, in WO 02/94 328 A2 and WO 02/94 329 A1.

It is optionally possible in a known manner to add a sulfonic acid derivative, including in a mixture with sulfite or sulfinic acid derivative, to the superabsorbent or else to the monomer mixture before or after drying, but preferably before drying. These mixtures are standard commercial products and are available, for example, in the form of mixtures of the sodium salt of 2-hydroxy-2-sulfinatoacetic acid, the disodium salt of 2-hydroxy-2-sulfonatoacetic acid and sodium bisulfite from L. Brüggemann KG (Salzstrasse 131, 74076 Heilbronn, Germany, www.brueggemann.com) under the BRÜGGOLIT® FF6M or BRÜGGOLIT® FF7 names, or alternatively BRUGGOLITE® FF6M or BRUGGOLITE® FF7. Preference is given to the use of the sulfonic acid derivatives in pure form. These too are standard commercial products. For example, the disodium salt of 2-hydroxy-2-sulfonatoacetic acid is available from L. Brüggemann KG (Salzstrasse 131, 74076 Heilbronn, Germany, www.brueggemann.com) under the BLANCOLEN® HP name.

The sulfonic acid derivative is generally used in an amount of at least 0.0001% by weight, preferably at least 0.001% by weight and more preferably at least 0.025% by weight, for example at least 0.05% by weight or at least 0.1% by weight, and generally at most 3% by weight, preferably at most 2% by weight and more preferably at most 0.5% by weight, for example at most 0.35% by weight or 0.2% by weight, based in each case on the total weight of the superabsorbent.

Just like the sulfonic acid derivative, it is optionally also possible in a known manner, in addition thereto or on its own, to add at least one phosphonic acid derivative to the superabsorbent or else to the monomer mixture before or after drying, but preferably before drying. Particular preference is given to the addition of preferably (1-hydroxyethane-1,1-diyl)bisphosphonic acid ("etidronic acid") or a salt thereof, especially the sodium salt, the potassium salt, the disodium salt, the dipotassium salt or the sodium potassium salt. Phosphonic acid derivatives of this kind are standard commercial products and are available, for example, under the Modosol® (formerly Cublen®) brand from Zschimmer & Schwarz Mohsdorf GmbH & Co KG, Chemnitztalstrasse 1, 09217 Burgstädt, Germany.

The phosphonic acid derivative is generally added in an amount of at least 0.01% by weight, preferably at least 0.1% by weight and more preferably at least 0.2% by weight, and generally at most 1.9% by weight, preferably at most 1.3% by weight and more preferably at most 0.6% by weight, based in each case on the total amount of the anhydrous superabsorbent.

The polymer gel obtained from the aqueous solution polymerization and optional subsequent neutralization is then preferably dried with a belt drier until the residual moisture content is preferably 0.5 to 15% by weight, more preferably 1 to 10% by weight and most preferably 2 to 8% by weight (see below for test method for the residual moisture or water content). In the case of too high a residual moisture content, the dried polymer gel has too low a glass transition temperature Tg and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the gel before drying is generally from 25 to 90% by weight, preferably from 30 to 80% by weight, more preferably from 35 to 70% by weight and most preferably from 40 to 60% by weight. Optionally, however, it is also possible to dry using a fluidized bed drier or a heatable mixer with a mechanical mixing unit, for example a paddle drier or a similar drier with mixing tools of different design. Optionally, the drier can be operated under nitrogen or another nonoxidizing inert gas or at least under reduced partial oxygen pressure in order to prevent oxidative yellowing processes. As a rule, however, sufficient aeration and removal of the steam will also lead to an acceptable product. In general, a minimum drying time is advantageous with regard to color and product quality.

During the drying, the residual monomer content in the polymer particles is also reduced, and last residues of the initiator are destroyed.

Thereafter, the dried polymer gel is optionally—and preferably—ground and classified, in which case the apparatus used for grinding may typically be single or multistage roll mills, preferably two- or three-stage roll mills, pin mills, hammer mills or vibratory mills. Oversize gel lumps which often still have not dried on the inside are elastomeric, lead to problems in the grinding and are preferably removed before the grinding, which can be done in a simple manner by wind sifting or by means of a sieve ("guard sieve" for the mill). In view of the mill used, the mesh size of the sieve should be selected such that a minimum level of disruption resulting from oversize, elastomeric particles occurs.

Excessively large, insufficiently finely ground superabsorbent particles are perceptible as coarse particles in their predominant use, in hygiene products such as diapers; they also lower the mean initial swell rate of the superabsorbent. Both are undesired. Advantageously, coarse-grain polymer particles are therefore separated from the product. This is done by conventional classification processes, for example wind sifting, or by sieving through a sieve with a mesh size of at most 1000 µm, preferably at most 900 µm, more preferably at most 850 µm and most preferably at most 800 µm. For example, sieves of mesh size 700 µm, 650 µm or 600 µm are used. The coarse polymer particles ("oversize") removed may, for cost optimization, be sent back to the grinding and sieving cycle or be processed further separately.

Polymer particles with too small a particle size lower the permeability (SFC). Advantageously, this classification therefore also removes fine polymer particles. If sieving is effected, this can conveniently be done through a sieve of mesh size at most 300 µm, preferably at most 200 µm, more preferably at most 150 µm and most preferably at most 100 µm. The fine polymer particles ("undersize" or "fines") removed can, for cost optimization, be sent back as desired to the monomer stream, to the polymerizing gel, or to the fully polymerized gel before the drying of the gel.

The mean particle size of the polymer particles removed as the product fraction is generally at least 200 µm, preferably at least 250 µm and more preferably at least 300 pm, and generally at most 600 µm and more preferably at most 500 µm. The proportion of particles with a particle size of at least 150 µm is generally at least 90% by weight, more preferably at least 95% by weight and most preferably at least 98% by weight. The proportion of particles with a particle size of at most 850 µm is generally at least 90% by weight, more preferably at least 95% by weight and most preferably at least 98% by weight.

In some other known production processes for superabsorbents, especially in the case of suspension polymerization, spray or dropletization polymerization, the selection of the process parameters defines the particle size distribution. These processes directly give rise to particulate superabsorbents of the desired particle size, such that grinding and sieving steps can often be dispensed with. In some processes (especially in the case of spray or dropletization polymerization), a dedicated drying step can often also be dispensed with.

The polymer thus prepared has superabsorbent properties and is covered by the term "superabsorbent". Its CRC is typically comparatively high, but its AUL or SFC comparatively low. A surface nonpostcrosslinked superabsorbent of this type is often referred to as "base polymer" to distinguish it from a surface postcrosslinked superabsorbent produced therefrom.

If no surface postcrosslinking takes place or the x-ray-amorphous aluminum hydroxide is added prior to the surface postcrosslinking, it is added to this base polymer as described above.

The base polymer is optionally surface postcrosslinked. Surface postcrosslinkers for superabsorbents and processes for surface postcrosslinking of superabsorbents are well-known. Suitable postcrosslinkers are compounds which comprise groups which can form bonds with at least two functional groups of the superabsorbent particles. In the case of the acrylic acid/sodium acrylate-based superabsorbents prevalent on the market, suitable surface postcrosslinkers are compounds which comprise groups which can form bonds with at least two carboxylate groups. Rather than "surface postcrosslinker" or "surface postcrosslinking", merely "postcrosslinker" or "postcrosslinking" are often also used.

Preferred surface postcrosslinkers are di- or triglycidyl compounds, for example glycidyl ethers, for instance ethylene glycol diglycidyl ether and glycerol di- or triglycidyl ether.

Preferred surface postcrosslinkers are also 2-oxazolidones such as 2-oxazolidone and N-(2-hydroxyethyl)-2-oxazolidone, N-methyl-2-oxazolidone, N-acyl-2-oxazolidones such as N-acetyl-2-oxazolidone, 2-oxotetrahydro-1,3-oxazine, bicyclic amide acetals such as 5-methyl-1-aza-4,6-dioxabicyclo[3.3.0]octane, 1-aza-4,6-dioxabicyclo[3.3.0]octane and 5-isopropyl-1-aza-4,6-dioxabicyclo[3.3.0]octane, bis-2-oxazolidones and poly-2-oxazolidones. Among these, particular preference is given to 2-oxazolidone, N-methyl-2-oxazolidone, N-(2-hydroxyethyl)-2-oxazolidone and N-hydroxypropyl-2-oxazolidone.

Further preferred postcrosslinkers are propane-1,3-diol, pentane-1,5-diol, hexane-1,6-diol and heptane-1,7-diol, butane-1,3-diol, octane-1,8-diol, nonane-1,9-diol and decane-1,10-diol. Among these, particular preference is given to those that are water-soluble at 23° C. to an extent of at least 30% by weight, preferably to an extent of at least 40% by weight, more preferably to an extent of at least 50% by weight, most preferably at least to an extent of 60% by weight, for example propane-1,3-diol and heptane-1,7-diol. Even more preferred are those that are liquid at 25° C.

Further preferred postcrosslinkers are butane-1,2,3-triol, butane-1,2,4-triol, glycerol, trimethylolpropane, trimethylolethane, pentaerythritol, 1- to 3-tuply (per molecule) ethoxylated glycerol, trimethylolethane or trimethylolpropane and 1- to 3-tuply (per molecule) propoxylated glycerol, trimethylolethane or trimethylolpropane. Additionally preferred are 2-tuply ethoxylated or propoxylated neopentyl glycol. Particular preference is given to 2-tuply and 3-tuply ethoxylated glycerol, neopentyl glycol, 2-methylpropane-1,3-diol and trimethylolpropane. Among these, particular preference is given to those that have a viscosity at 23° C. of less than 3000 mPas, preferably less than 1500 mPas, more preferably less than 1000 mPas, especially preferably less than 500 mPas and very especially preferably less than 300 mPas.

Further preferred postcrosslinkers are ethylene carbonate and propylene carbonate.

A further preferred postcrosslinker is 2,2'-bis(2-oxazoline).

Likewise preferred postcrosslinkers are oxetanes, especially 3-ethyloxetane-3-methanol or 3,3'-[oxybis(methylene)]bis[(3-ethyl)oxetane].

These preferred postcrosslinkers minimize side reactions and subsequent reactions which lead to volatile and hence malodorous compounds. The superabsorbents produced with the preferred postcrosslinkers are therefore odor-neutral even in the moistened state.

It is possible to use an individual postcrosslinker or any desired mixtures of different postcrosslinkers.

The postcrosslinker is generally used in an amount of at least 0.001% by weight, preferably of at least 0.02% by weight, more preferably of at least 0.05% by weight, and generally at most 2% by weight, preferably at most 1% by weight, more preferably at most 0.3% by weight, for example at most 0.15% by weight or at most 0.095% by weight, based in each case on the mass of the base polymer contacted therewith (for example the sieve fraction in question).

The postcrosslinking is typically performed in such a way that a solution of the postcrosslinker is sprayed onto the dried base polymer particles. After the spray application, the polymer particles coated with postcrosslinker are dried thermally, and the postcrosslinking reaction can take place either before or during the drying. If surface postcrosslinkers with polymerizable groups are used, the surface postcrosslinking can also be effected by means of free-radically induced polymerization of such groups by means of common free-radical formers or else by means of high-energy radiation, for example UV light. This can be done in parallel with or instead of the use of postcrosslinkers which form covalent or ionic bonds to functional groups at the surface of the base polymer particles.

The spray application of the postcrosslinker solution is preferably carried out in mixers with moving mixing tools, such as screw mixers, disk mixers, paddle mixers or shovel mixers, or mixers with other mixing tools. Particular preference is given, however, to vertical mixers. It is also possible to spray on the postcrosslinker solution in a fluidized bed. Suitable mixers are obtainable, for example, as Pflugschar® (plowshare) mixers from Gebr. Lödige Maschinenbau GmbH, Elsener-Strasse 7-9, 33102 Paderborn, Germany, or as Schugi® Flexomix® mixers, Vrieco-Nauta® mixers or Turbulizer® mixers from Hosokawa Micron BV, Gildenstraat 26, 7000 AB Doetinchem, the Netherlands.

The spray nozzles usable are not subject to any restriction. Suitable nozzles and atomization systems are described, for example, in the following references: Zerstäuben von Flüssigkeiten [Atomization of Liquids], Expert-Verlag, vol. 660, Reihe Kontakt & Studium, Thomas Richter (2004) and in Zerstäubungstechnik [Atomization Technology], Springer-Verlag, VDI-Reihe, Günter Wozniak (2002). It is possible to use mono- and polydisperse spray systems. Among the polydisperse systems, one-phase pressurized nozzles (jet- or lamella-forming), rotary atomizers, two-phase atomizers, ultrasound atomizers and impingement nozzles are suitable. In the case of the two-phase atomizers, the liquid phase can be mixed with the gas phase either internally or externally. The spray profile of the nozzles is uncritical and may assume any desired form, for example a round jet, flat jet, wide angle round jet or circular ring spray profile. It is advantageous to use a nonoxidizing gas if two-phase atomizers are used, particular preference being given to nitrogen, argon or carbon dioxide. The liquid to be sprayed can be supplied to such nozzles under pressure. The atomization of the liquid to be sprayed can be effected by expanding it in the nozzle bore on attainment of a particular minimum velocity. In addition, it is also possible to use one-phase nozzles for the inventive purpose, for example slit nozzles or swirl chambers (full-cone nozzles) (for example from Düsen-Schlick GmbH, Germany, or from Spraying Systems Germany GmbH, Germany). Such nozzles are also described in EP 0 534 228 A1 and EP 1 191 051 A2.

The postcrosslinkers are typically used in the form of an aqueous solution. If exclusively water is used as the solvent, a surfactant or deagglomeration assistant is advantageously added to the postcrosslinker solution or actually to the base polymer. This improves the wetting characteristics and reduces the tendency to form lumps.

All anionic, cationic, nonionic and amphoteric surfactants are suitable as deagglomeration assistants, but preference is given to nonionic and amphoteric surfactants for skin compatibility reasons. The surfactant may also comprise nitrogen. For example, sorbitan monoesters, such as sorbitan monococoate and sorbitan monolaurate, or ethoxylated variants thereof, for example Polysorbat 20®, are added. Further suitable deagglomeration assistants are the ethoxylated and alkoxylated derivatives of 2-propylheptanol, which are sold under the Lutensol XL® and Lutensol XP® brands (BASF SE, Carl-Bosch-Strasse 38, 67056 Ludwigshafen, Germany).

The deagglomeration assistant can be metered in separately or added to the postcrosslinker solution. Preference is given to simply adding the deagglomeration assistant to the postcrosslinker solution.

The amount of the deagglomeration assistant used, based on base polymer, is, for example, 0% to 0.1% by weight, preferably 0% to 0.01% by weight, more preferably 0% to 0.002% by weight. The deagglomeration assistant is preferably metered in such that the surface tension of an aqueous extract of the swollen base polymer and/or of the swollen postcrosslinked water-absorbing polymer at 23° C. is at least 0.060 N/m, preferably at least 0.062 N/m, more preferably at least 0.065 N/m, and advantageously at most 0.072 N/m.

The aqueous postcrosslinker solution may, as well as the at least one postcrosslinker, also comprise a cosolvent. The content of nonaqueous solvent or total amount of solvent can be used to adjust the penetration depth of the postcrosslinker into the polymer particles. Industrially readily available cosolvents are C1-C6 alcohols such as methanol, ethanol, n-propanol, isopropanol, n-butanol, sec-butanol, tert-butanol or 2-methyl-1-propanol, $C_2$-$C_5$ diols such as ethylene glycol, 1,2-propylene glycol or butane-1,4-diol, ketones such as acetone, or carboxylic esters such as ethyl acetate. A disadvantage of some of these cosolvents is that they have typical intrinsic odors.

The cosolvent itself is ideally not a postcrosslinker under the reaction conditions. However, it may arise in the boundary case and depending on the residence time and temperature that the cosolvent contributes partly to crosslinking. This is the case especially when the postcrosslinker is relatively slow to react and can therefore also constitute its own cosolvent, as is the case, for example, when cyclic carbonates, diols or polyols are used. Such postcrosslinkers can also be used in the function as a cosolvent in a mixture with more reactive postcrosslinkers, since the actual postcrosslinking reaction can then be performed at lower temperatures and/or with shorter residence times than in the absence of the more reactive crosslinker. Since the cosolvent is used in relatively large amounts and some also remains in the product, it must not be toxic.

In the process of the invention, the abovementioned diols and polyols and also the cyclic carbonates are also suitable as cosolvents. They fulfill this function in the presence of a comparatively reactive postcrosslinker and/or of a di- or triglycidyl compound. Preferred cosolvents in the process of the invention are, however, especially the diols mentioned, especially when a reaction of the hydroxyl groups is sterically hindered by neighboring groups. Although such diols are also suitable in principle as postcrosslinkers, this requires significantly higher reaction temperatures or optionally higher use amounts than for sterically unhindered diols.

Particularly preferred combinations of low-reactivity postcrosslinker as a cosolvent and reactive postcrosslinker are combinations of the polyhydric alcohols, diols and polyols mentioned with the stated amide acetals or carbamates. Suitable combinations are, for example, 2-oxazolidone/propane-1,2-diol and N-(2-hydroxyethyl)-2-oxazolidone/propane-1,2-diol, and also ethylene glycol diglycidyl ether/propane-1,2-diol. Very particularly preferred combinations are 2-oxazolidone/propane-1,3-diol and N-(2-hydroxyethyl)-2-oxazolidone/propane-1,3-diol. Further preferred combinations are those with ethylene glycol diglycidyl ether or glyceryl di- or triglycidyl ether with the following solvents, cosolvents or cocrosslinkers: isopropanol, propane-1,3-diol, 1,2-propylene glycol or mixtures thereof. Further preferred combinations are those with 2-oxazolidone or (2-hydroxyethyl)-2-oxazolidone in the following solvents, cosolvents or cocrosslinkers: isopropanol, propane-1,3-diol, 1,2-propylene glycol, ethylene carbonate, propylene carbonate or mixtures thereof.

Frequently, the concentration of the cosolvent in the aqueous postcrosslinker solution is from 15 to 50% by weight, preferably from 15 to 40% by weight and more preferably from 20 to 35% by weight, based on the postcrosslinker solution. In the case of cosolvents which have only limited miscibility with water, the aqueous postcrosslinker solution will advantageously be adjusted such that only one phase is present, optionally by lowering the concentration of the cosolvent.

In a preferred embodiment, no cosolvent is used. The postcrosslinker is then employed only as a solution in water, optionally with addition of a deagglomeration assistant.

The concentration of the at least one postcrosslinker in the aqueous postcrosslinker solution is typically from 1 to 20% by weight, preferably from 1.5 to 10% by weight and more preferably from 2 to 5% by weight, based on the postcrosslinker solution.

The total amount of the postcrosslinker solution based on base polymer is typically from 0.3 to 15% by weight and preferably from 2 to 6% by weight.

The actual surface postcrosslinking by reaction of the surface postcrosslinker with functional groups at the surface of the base polymer particles is usually carried out by heating the base polymer wetted with surface postcrosslinker solution, typically referred to as "drying" (but not to be confused with the above-described drying of the polymer gel from the polymerization, in which typically very much more liquid has to be removed). The drying can be effected in the mixer itself, by heating the jacket, by means of heat exchange surfaces or by blowing in warm gases. Simultaneous admixing of the superabsorbent with surface postcrosslinker and drying can be effected, for example, in a fluidized bed drier. The drying is, however, usually carried out in a downstream drier, for example a tray drier, a rotary tube oven, a paddle or disk drier or a heatable screw. Suitable driers are obtainable, for example, as Solidair® or Torusdisc® driers from Bepex International LLC, 333 N.E. Taft Street, Minneapolis, MN 55413, U.S.A., or as paddle or shovel driers or else as fluidized bed driers from Nara Machinery Co., Ltd., European office, Europaallee 46, 50226 Frechen, Germany.

It is possible to heat the polymer particles by means of contact surfaces in a downstream drier for the purpose of drying and performing the surface postcrosslinking, or by means of warm inert gas supply, or by means of a mixture of one or more inert gases with steam, or only with steam alone. In the case of supply of the heat by means of contact surfaces, it is possible to perform the reaction under inert gas at slightly or completely reduced pressure. In the case of use of steam for direct heating of the polymer particles, it is desirable in accordance with the invention to operate the drier under standard pressure or elevated pressure. In this case, it may be advisable to split up the postcrosslinking step into a heating step with steam and a reaction step under inert gas but without steam. This can be achieved in one or more apparatuses. According to the invention, the polymer particles can be heated with steam as early as in the postcrosslinking mixer. The base polymer used may still have a temperature of from 10 to 120° C. from preceding process steps; the postcrosslinker solution may have a temperature of from 0 to 70° C. In particular, the postcrosslinker solution can be heated to reduce the viscosity.

Preferred drying temperatures are in the range of 100 to 250° C., preferably 120 to 220° C., more preferably 130 to 210° C. and most preferably 150 to 200° C. The preferred residence time at this temperature in the reaction mixer or dryer is preferably at least 10 minutes, more preferably at least 20 minutes, most preferably at least 30 minutes, and typically at most 60 minutes. Typically, the drying is conducted such that the superabsorbent has a residual moisture content of generally at least 0.1% by weight, preferably at least 0.2% by weight and most preferably at least 0.5% by weight, and generally at most 15% by weight, preferably at most 10% by weight and more preferably at most 8% by weight.

The postcrosslinking can take place under standard atmospheric conditions. "Standard atmospheric conditions" means that no technical precautions are taken in order to reduce the partial pressure of oxidizing gases, such as that of the atmospheric oxygen, in the apparatus in which the postcrosslinking reaction predominantly takes place (the "postcrosslinking reactor", typically the drier). However, preference is given to performing the postcrosslinking reaction under reduced partial pressure of oxidizing gases. Oxidizing gases are substances which, at 23° C., have a vapor pressure of at least 1013 mbar and act as oxidizing agents in combustion processes, for example oxygen, nitrogen oxide and nitrogen dioxide, especially oxygen. The partial pressure of oxidizing gases is preferably less than 140 mbar, preferably less than 100 mbar, more preferably less than 50 mbar and most preferably less than 10 mbar. When the thermal postcrosslinking is carried out at ambient pressure, i.e. at a total pressure around 1013 mbar, the total partial pressure of the oxidizing gases is determined by their proportion by volume. The proportion of the oxidizing gases is preferably less than 14% by volume, preferably less than 10% by volume, more preferably less than 5% by volume and most preferably less than 1% by volume.

The postcrosslinking can be carried out under reduced pressure, i.e. at a total pressure of less than 1013 mbar. The total pressure is typically less than 670 mbar, preferably less than 480 mbar, more preferably less than 300 mbar and most preferably less than 200 mbar. When drying and postcrosslinking are carried out under air with an oxygen content of 20.8% by volume, the partial oxygen pressures corresponding to the abovementioned total pressures are 139 mbar (670 mbar), 100 mbar (480 mbar), 62 mbar (300 mbar) and 42 mbar (200 mbar), the respective total pressures being in the brackets. Another means of lowering the partial pressure of oxidizing gases is the introduction of nonoxidizing gases, especially inert gases, into the apparatus used for postcrosslinking. Suitable inert gases are substances that are in gaseous form in the postcrosslinking drier at the postcrosslinking temperature and the given pressure and do not have an oxidizing action on the constituents of the drying polymer particles under these conditions, for example nitrogen, carbon dioxide, argon, steam, preference being given to nitrogen. The amount of inert gas is generally from 0.0001 to 10 $m^3$, preferably from 0.001 to 5 $m^3$, more preferably from 0.005 to 1 $m^3$ and most preferably from 0.005 to 0.1 $m^3$, based on 1 kg of superabsorbent.

In the process of the invention, the inert gas, if it does not comprise steam, can be blown into the postcrosslinking drier via nozzles; however, particular preference is given to adding the inert gas to the polymer particle stream via nozzles actually within or just upstream of the mixer, by admixing the superabsorbent with surface postcrosslinker.

It will be appreciated that vapors of cosolvents removed from the drier can be condensed again outside the drier and optionally recycled.

One way of adding the x-ray-amorphous aluminum hydroxide during the surface postcrosslinking is mixing-in during the surface postcrosslinking reaction by addition to an apparatus used for the surface postcrosslinking reaction if the contents are mixed in this apparatus. Suitable apparatuses are, for instance, the apparatuses mentioned above for the purpose except for the tray drier. Preference is given to using paddle and shovel driers for the purpose.

Before, during or after the postcrosslinking, in addition to the organic postcrosslinkers mentioned that form covalent bonds with carboxyl groups in the superabsorbent and in addition to the x-ray-amorphous aluminum hydroxide, polyvalent metal ions are optionally applied to the surfaces of the superabsorbent of the invention, or, if no surface postcrosslinking with one of the organic postcrosslinkers mentioned is conducted, in lieu thereof. As already stated above, this application of polyvalent metal ions is in principle an (optionally additional) surface postcrosslinking by ionic, noncovalent bonds and is referred to in the context of this invention, for distinction from surface postcrosslinking by means of covalent bonds, as "complexation" with the metal ions in question.

This application of polyvalent cations is typically effected by spray application of solutions of di-or polyvalent cations, usually di-, tri- or tetravalent metal cations, but also polyvalent cations such as polymers formed, in a formal sense, entirely or partly from vinylamine monomers, such as partly or fully hydrolyzed polyvinylamide (so-called "polyvinylamine"), whose amine groups are always—even at very high pH values—present partly in protonated form to give ammonium groups. Examples of usable divalent metal cations are especially the divalent cations of metals of groups 2 (especially Mg, Ca, Sr, Ba), 7 (especially Mn), 8 (especially Fe), 9 (especially Co), 10 (especially Ni), 11 (especially Cu) and 12 (especially Zn) of the Periodic Table of the Elements. Examples of usable trivalent metal cations are especially the trivalent cations of metals of groups 3 including the lanthanides (especially Sc, Y, La, Ce), 8 (especially Fe), 11 (especially Au), 13 (especially Al) and 14 (especially Bi) of the Periodic Table of the Elements. Examples of usable tetravalent cations are especially the tetravalent cations of metals from the lanthanides (especially Ce) and group 4 (especially Ti, Zr, Hf) of the Periodic Table of the Elements. The metal cations can be used either alone or as a mixture with one another. Particular preference is given to the use of trivalent metal cations. Very particular preference is given to the use of aluminum cations.

Among the metal cations mentioned, suitable metal salts are all of those which possess sufficient solubility in the solvent to be used. Particularly suitable metal salts are those with weakly complexing anions, for example chloride, nitrate and sulfate, hydrogensulfate, carbonate, hydrogencarbonate, nitrate, phosphate, hydrogenphosphate, or dihydrogenphosphate. Preference is given to salts of mono- and dicarboxylic acids, hydroxy acids, keto acids and amino acids, or basic salts. Preferred examples include acetates, propionates, tartrates, maleates, citrates, lactates, malates, succinates. Likewise preferred is the use of hydroxides, provided that they are soluble. Particular preference is given to the use of 2-hydroxycarboxylic salts such as citrates and lactates. Examples of particularly preferred metal salts are alkali metal and alkaline earth metal aluminates and hydrates thereof, for instance sodium aluminate and hydrates thereof, alkali metal and alkaline earth metal lactates and citrates and hydrates thereof, aluminum acetate, aluminum propionate, aluminum citrate and aluminum lactate.

The cations and salts mentioned can be used in pure form or as a mixture of different cations or salts. The salts of the di- and/or trivalent metal cation used may comprise further secondary constituents such as still unneutralized carboxylic acid and/or alkali metal salts of the neutralized carboxylic acid. Preferred alkali metal salts are those of sodium and potassium, and those of ammonium. They are typically used in the form of an aqueous solution which is obtained by dissolving the solid salts in water, or is preferably obtained directly as such, which avoids any drying and purification steps. It is advantageously also possible to use the hydrates of the salts mentioned, which often dissolve more rapidly in water than the anhydrous salts.

The amount of metal salt used is generally at least 0.001% by weight, preferably at least 0.01% by weight and more preferably at least 0.1% by weight, for example at least 0.4% by weight, and generally at most 5% by weight, preferably at most 2.5% by weight and more preferably at most 1% by weight, for example at most 0.7% by weight, based in each case on the mass of the base polymer.

The salt of the trivalent metal cation can be used in the form of a solution or suspension. Solvents used for the metal salts may be water, alcohols, DMF, DMSO and mixtures of these components. Particular preference is given to water and water/alcohol mixtures, for example water/methanol, water/propane-1,2-diol and water/propane-1,3-diol.

The treatment of the base polymer with solution of a di- or polyvalent cation is effected in the same manner as that with surface postcrosslinker, including the drying step. Surface postcrosslinker and polyvalent cation can be sprayed on in a combined solution or as separate solutions. The spray application of the metal salt solution to the superabsorbent particles may either precede or follow the surface postcrosslinking. In a particularly preferred process, the spray application of the metal salt solution is effected in the same step together with the spray application of the crosslinker solution, in which case the two solutions are sprayed on separately in succession or simultaneously via two nozzles, or crosslinker solution and metal salt solution can be sprayed on jointly via one nozzle.

It is also possible to add all further additives known in the surface postcrosslinking of superabsorbents. Examples are basic salts of a divalent metal cation such as calcium or strontium, usually in the form of hydroxides, hydrogencarbonates, carbonates, acetates, propionates, citrates, gluconates, lactates, tartrates, malates, succinates, maleates and/or fumarates. Further examples are reducing compounds such as hypophosphites, phosphonic acid derivatives, sulfinates or sulfites.

More preferably, aside from the addition of x-ray-amorphous aluminum hydroxide, no further polyvalent metal ions are added.

If a drying step is carried out after the surface postcrosslinking and/or treatment with complexing agent, it is advantageous but not absolutely necessary to cool the product after the drying. The cooling can be effected continuously or batchwise; to this end, the product is conveniently conveyed continuously into a cooler arranged downstream of the drier. Any apparatus known for removal of heat from pulverulent solids can be used for this purpose, more particularly any device mentioned above as drying apparatus, except that it is charged not with a heating medium but with a cooling medium, for example with cooling water, such that no heat is introduced into the superabsorbent via the walls and, according to the construction, also via the stirring elements or other heat exchange surfaces, and is instead removed therefrom.

Preference is given to the use of coolers in which the product is moved, i.e. cooled mixers, for example shovel coolers, disk coolers or paddle coolers. The superabsorbent can also be cooled in a fluidized bed by injecting a cooled gas such as cold air. The cooling conditions are adjusted so as to obtain a superabsorbent with the temperature desired for further processing. Typically, a mean residence time in the cooler of generally at least 1 minute, preferably at least 3 minutes and more preferably at least 5 minutes, and generally at most 6 hours, preferably at most 2 hours and more preferably at most 1 hour is established, and the cooling performance is such that the product obtained has a temperature of generally at least 0° C., preferably at least 10° C. and more preferably at least 20° C., and generally at most 100° C., preferably at most 80° C. and more preferably at most 60° C.

The surface postcrosslinked superabsorbent is optionally ground and/or sieved in a customary manner. Grinding is typically not required here, but the removal by sieving of agglomerates or fines formed is usually appropriate for establishment of the desired particle size distribution of the product. Agglomerates and fines are either discarded or preferably recycled into the process in a known manner at a suitable point, agglomerates after comminution. The particle sizes desired for surface postcrosslinked superabsorbents are the same as for base polymers.

If x-ray-amorphous aluminum hydroxide is added after a surface postcrosslinking, this can conveniently be done in the downstream cooler, but also in a dedicated mixing apparatus. The x-ray-amorphous aluminum hydroxide can be added in each case either before or after a sieving and grinding step that follows a surface postcrosslinking operation.

Optionally, the superabsorbents of the invention that have been produced by the process of the invention are provided with further additions, nonlimiting examples being those that provide stabilization against discoloration, reduce the tendency to caking or further increase the permeability. For this purpose, all known additives can be used in the manner known for each in the process of the invention. Examples of known additions that provide stabilization against discoloration are the abovementioned sulfonic acid or phosphonic acid derivatives, which can also be applied after the production of the superabsorbent of the invention rather than or as well as the addition during the production thereof. Examples of known additions that reduce the caking tendency of the superabsorbent or further increase the permeability are water-insoluble inorganic powders.

Usually, the x-ray-amorphous aluminum hydroxide added in accordance with the invention will also sufficiently reduce the caking tendency of the superabsorbent. If the amount added in accordance with the invention is insufficient for this purpose, it can also be increased above the abovementioned limits to the extent that the desired reduction in the caking tendency is achieved. This additional amount of x-ray-amorphous aluminum hydroxide can also be added in a second portion, like other water-soluble inorganic powders as well. Typically, the additional amount of x-ray-amorphous aluminum hydroxide is at least as large as the other water-insoluble inorganic powders.

If a further inorganic powder is added, more preferably, precipitated silicon dioxide or silicon dioxide produced by pyrolysis and aluminum oxide produced by pyrolysis is used. Pyrogenic silicon dioxide is available, for example, under the AEROSIL® brand, and pyrogenic aluminum oxide, for example, under the AEROXIDE® Alu brand from Evonik Industries AG, Inorganic Materials, Rodenbacher Chaussee 4, 63457 Hanau-Wolfgang, Germany. Silicon dioxide produced by precipitation is available, for example, under the SIPERNAT® brand from Evonik Industries AG, Inorganic Materials, Rodenbacher Chaussee 4, 63457 Hanau-Wolfgang, Germany. The water-insoluble inorganic powders can also be hydrophobized by suitable surface treatment and are often supplied by manufacturers both in hydrophobized and in hydrophilic form. In the context of this invention, the use of hydrophilic water-insoluble inorganic powders is preferred.

In general, the water-insoluble inorganic powder is added to the superabsorbent in an amount of at least 0.005% by weight, preferably of at least 0.03% by weight and more preferably of at least 0.05% by weight, and generally of at most 6.0% by weight, preferably at most 1.0% by weight and more preferably at most 0.5% by weight, based in each case on the total weight of the anhydrous superabsorbent comprising inorganic powder.

Superabsorbents can be mixed with the optional additives by any known mixing process. When in solid form, they are incorporated by mixing in substance or as a suspension in a solvent or suspension medium, and, when in dissolved or liquid form, optionally also in solution or liquid form. Due to easier homogeneous distribution, the additives are preferably incorporated into the superabsorbent by mixing as a powder or suspension. This does not necessarily produce a physical mixture separable in a simple manner by mechanical measures. The additives may quite possibly enter into a more definite bond with the superabsorbent, for example in the form of a comparatively firmly adhering surface layer or in the form of particles adhering firmly to the surface of the superabsorbent particles. The mixing of the additives into the known superabsorbent can quite possibly also be understood and referred to as "coating".

If a solution or suspension is used for coating, the solvent or suspension medium used is a solvent or suspension medium which is chemically compatible both with the superabsorbent and with the additive, i.e. does not enter into any undesired chemical reactions therewith. Typically, water or an organic solvent is used, for example an alcohol or polyol, or mixtures thereof. Examples of suitable solvents or suspension media are water, isopropanol/water, propane-1,3-diol/water and propylene glycol/water, where the mixing ratio by mass is preferably from 20:80 to 40:60. If a suspension medium is used for the stabilizers to be used in accordance with the invention or the inorganic particulate solid, water is preferred. A surfactant can be added to the solution or suspension.

Optional additives are, if they are not added to the monomer mixture or the polymerizing gel, generally mixed with the superabsorbent in exactly the same way as the solution or suspension which comprises a surface postcrosslinker and is applied to the superabsorbent for surface postcrosslinking. The additive can be applied as a constituent of the solution applied for surface postcrosslinking or of one of the components thereof to an (as yet) nonpostcrosslinked superabsorbent (a "base polymer"), i.e. the additive is added to the solution of the surface postcrosslinker or to one of the components thereof. The superabsorbent coated with surface postcrosslinker and additives then passes through the further process steps required for surface postcrosslinking, for example a thermally induced reaction of the surface postcrosslinker with the superabsorbent. This process is comparatively simple and economically viable.

If the superabsorbent is subjected to a cooling step after the surface postcrosslinking or the complexation, the optional additions can conveniently be mixed in in the cooler. If additives are applied as a solution or suspension, they can also be applied to the already surface postcrosslinked superabsorbent in the same mixing apparatuses as described for the application of the surface postcrosslinker to the base polymer. Usually, but not necessarily, this is followed by heating, just like in the surface postcrosslinking step, in order to dry the superabsorbent again. The temperature established in this drying operation is then, however, generally at most 110° C., preferably at most 100° C. and more preferably at most 90° C., in order to prevent undesired reactions of the additive. The temperature is adjusted such that, in view of the residence time in the drying unit, the desired water content of the superabsorbent is achieved. It is also entirely possible and convenient to add additives individually or together with other customary assistants, for example dust binders, anticaking agents or water for remoisturization of the superabsorbent. The temperature of the polymer particles in this case is between 0° C. and 190° C., preferably less than 160° C., more preferably less than 130° C., even more preferably less than 100° C. and most preferably less than 70° C. The polymer particles are optionally cooled rapidly after coating to temperatures below any decomposition temperature of the additive.

It is optionally possible to additionally apply to the surface of the superabsorbent particles, whether unpostcrosslinked or postcrosslinked, in any process step of the preparation process, if required, all known coatings, such as film-forming polymers, thermoplastic polymers, dendrimers, polycationic polymers (for example polyvinylamine, polyethyleneimine or polyallylamine), or all water-soluble mono- or polyvalent metal salts known to those skilled in the art, for example aluminum sulfate, sodium salts, potassium salts, zirconium salts or iron salts. Examples of useful alkali metal salts are sodium and potassium sulfate, and sodium and potassium lactates, citrates and sorbates. This allows additional effects, for example a reduced caking tendency of the end product or of the intermediate in the particular process step of the production process, improved processing properties or a further enhanced permeability (SFC), to be achieved. When additives are used and sprayed on in the form of dispersions, they are preferably used in the form of aqueous dispersions, and preference is given to additionally applying an antidusting agent to fix the additive on the surface of the superabsorbent. The antidusting agent is then either added directly to the dispersion of the inorganic pulverulent additive; optionally, it can also be added as a separate solution before, during or after the application of the inorganic pulverulent additive by spray application. Most preferred is the simultaneous spray application of postcrosslinking agent, antidusting agent and pulverulent inorganic additive in the postcrosslinking step. In a further preferred process variant, the antidusting agent is, however, added separately in the cooler, for example by spray application from above, below or from the side. Particularly suitable antidusting agents which can also serve to fix pulverulent inorganic additives on the surface of the water-absorbing polymer particles are polyethylene glycols with a molecular weight of 400 to 20 000 g/mol, polyglycerol, 3- to 100-tuply ethoxylated polyols, such as trimethylolpropane, glycerol, sorbitol and neopentyl glycol. Particularly suitable are 7- to 20-tuply ethoxylated glycerol or trimethylolpropane, for example Polyol TP 70° (Perstorp, Sweden). The latter have the advantage, more particularly, that they lower the surface tension of an aqueous extract of the water-absorbing polymer particles only insignificantly.

It is likewise possible to adjust the superabsorbent of the invention to a desired water content by adding water. It may also be advantageous to slightly swell the superabsorbent by addition of water and then adjust it back to the desired water content by drying.

All coatings, solids, additives and assistants can each be added in separate process steps, but the most convenient method is usually to add them—if they are not added during the admixing of the base polymer with surface postcrosslinking agent—to the superabsorbent in the cooler, for instance by spray application of a solution or addition in fine solid form or in liquid form.

The superabsorbents of the invention generally have a centrifuge retention capacity (CRC, for test method see below) of at least 5 g/g, preferably of at least 10 g/g and more preferably of at least 20 g/g. Typically, it is not more than 40 g/g for surface postcrosslinked superabsorbents, but it is often higher for base polymers.

The superabsorbents of the invention, if they have been surface postcrosslinked, typically have an absorption under load (AUL0.9 psi, for test method see below) of at least 10 g/g, preferably at least 14 g/g, more preferably at least 18 g/g and most preferably at least 22 g/g, and typically not more than 30 g/g.

The present invention further provides hygiene articles comprising superabsorbent of the invention, preferably ultrathin diapers, comprising an absorbent layer consisting of 50 to 100% by weight, preferably 60 to 100% by weight, more preferably 70 to 100% by weight, especially preferably 80 to 100% by weight and very especially preferably 90 to 100% by weight of superabsorbent of the invention, of course not including the envelope of the absorbent layer.

Very particularly advantageously, the superabsorbents of the invention are also suitable for production of laminates and composite structures, as described, for example, in US 2003/0181115 and US 2004/0019342. In addition to the hotmelt adhesives described in both documents for production of such novel absorbent structures, and especially the fibers, described in US 2003/0181115, composed of hotmelt adhesives to which the superabsorbent particles are bound, the superabsorbents of the invention are also suitable for production of entirely analogous structures using UV-crosslinkable hotmelt adhesives, which are sold, for example, as AC-Resin® (BASF SE, Ludwigshafen, Germany). These UV-crosslinkable hotmelt adhesives have the advantage of already being processible at 120 to 140° C.; they therefore have better compatibility with many thermoplastic substrates. A further significant advantage is that UV-crosslinkable hotmelt adhesives are very benign in toxicological terms and also do not cause any vaporization in the hygiene articles. A very significant advantage in connection with the superabsorbents of the invention is the property of the UV-crosslinkable hotmelt adhesives of lacking any tendency to yellow during processing and crosslinking. This is especially advantageous when ultrathin or partly transparent hygiene articles are to be produced. The combination of the superabsorbents of the invention with UV-crosslinkable hotmelt adhesives is therefore particularly advantageous. Suitable UV-crosslinkable hotmelt adhesives are described, for example, in EP 0 377 199 A2, EP 0 445 641 A1, U.S. Pat. No. 5,026,806, EP 0 655 465 A1 and EP 0 377 191 A2.

The superabsorbent of the invention can also be used in other fields of industry in which fluids, especially water or aqueous solutions, are absorbed. These fields are, for example, storage, packaging, transport (as constituents of packaging material for water- or moisture-sensitive articles, for instance for flower transport, and also as protection against mechanical effects); animal hygiene (in cat litter); food packaging (transport of fish, fresh meat; absorption of water, blood in fresh fish or meat packaging); medicine (wound plasters, water-absorbing material for burn dressings, or for other weeping wounds), cosmetics (carrier material for pharmaceutical chemicals and medicaments, rheumatic plasters, ultrasonic gel, cooling gel, cosmetic thickeners, sunscreen); thickeners for oil/water or water/oil emulsions; textiles (moisture regulation in textiles, shoe insoles, for evaporative cooling, for instance in protective clothing, gloves, headbands); chemical engineering applications (as a catalyst for organic reactions, for immobilization of large functional molecules such as enzymes, as an adhesive in agglomerations, heat stores, filtration aids, hydrophilic components in polymer laminates, dispersants, liquefiers); as assistants in powder injection molding, in the building and construction industry (installation, in loam-based renders, as a vibration-inhibiting medium, assistants in tunnel excavations in water-rich ground, cable sheathing); water treatment, waste treatment, water removal (deicers, reusable sand bags); cleaning; agrochemical industry (irrigation, retention of melt water and dew deposits, composting additive, protection of forests from fungal/insect infestation, retarded release of active ingredients to plants); for firefighting or for fire protection; coextrusion agents in thermoplastic polymers (for example for hydrophilization of multilayer films); production of films and thermoplastic moldings which can absorb water (e.g. films which store rain and dew for agriculture; films comprising superabsorbents for maintaining freshness of fruit and vegetables which are packaged in moist films; superabsorbent-polystyrene coextrudates, for example for packaging foods such as meat, fish, poultry, fruit and vegetables); or as a carrier substance in active ingredient formulations (pharmaceuticals, crop protection).

The articles of the invention for absorption of fluid differ from known examples in that they comprise the superabsorbent of the invention.

A process for producing articles for absorption of fluid, especially hygiene articles, has also been found, said process comprising using at least one superabsorbent of the invention in the production of the article in question. In addition, processes for producing such articles using superabsorbents are known.

Test Methods

The superabsorbent is tested by the test methods described below.

The standard test methods described hereinafter and designated "NWSP" are described in: "Nonwovens Standards Procedures", 2015 edition, published jointly by EDANA (European Disposables and Nonwovens Association, Avenue Herrmann Debroux 46, 1160 Brussels, Belgium, www.edana.org) and INDA (Association of the Nonwoven Fabrics Industry, 1100 Crescent Green, Suite 115, Cary, North Carolina 27518, U.S.A., www.inda.org). This publication is obtainable both from EDANA and from INDA.

All measurements described below should, unless stated otherwise, be conducted at an ambient temperature of 23±2° C. and a relative air humidity of 50±10%. The superabsorbent particles are mixed thoroughly before the measurement unless stated otherwise.

Centrifuge Retention Capacity (CRC)

The centrifuge retention capacity of the superabsorbent is determined by the method described in US 2007/0 135 785 A1.

Absorbency Under a Load of 0.9 psi (AUL0.9 psi)

The absorbency under a load of 6205 Pa (0.9 psi) (AUL0.9 psi) of the superabsorbent is determined by the method described in US 2014/0 306 156 A1.

Absorbency Under a Load of 0.3 psi (AUL0.3 psi)

The absorbency under a load of 2068 Pa (0.3 psi) (AUL0.3 psi) of the superabsorbent is determined by standard test method No. NWSP 242.0 R2 (15) "Gravimetric Determination of Absorption Against Pressure", but with a weight (see point 6.5 of the method description) with which a pressure of 2068 Pa rather than 4826 Pa is established (corresponding to 21 g/cm² rather than 49 g/cm²).

Volumetric Absorbency Under Load (VAUL)

The volumetric absorbency under load of the superabsorbent is determined by the method described in US 2015/0 299 404 A1. Table 1 reports the τ value ascertained at a pressure of 2068 Pa (0.3 psi).

Moisture Content of the Superabsorbent (Residual Moisture, Water Content)

The water content of the superabsorbent is determined by standard test method No. NWSP 230.0 R2 (15) "Estimation of the Moisture Content as Weight Loss Upon Heating".

Particle Size Distribution

The particle size distribution of the superabsorbent is determined by standard test method No. NWSP 220.0 R2 (15) "Determination of Polyacrylate Superabsorbent Powders and Particle Size Distribution—Sieve Fractionation".

Extractables

The extractables in the superabsorbent are determined by standard test method No. NWSP 270.0 R2 (15) "Determination of Extractable Polymer Content by Potentiometric Titration".

Permeability (SFC, "Saline Flow Conductivity")

The permeability of a swollen gel layer formed by the superabsorbent as a result of liquid absorption is determined under a pressure of 0.3 psi (2068 Pa), as described in EP 0 640 330 A1, as the gel layer permeability of a swollen gel layer of superabsorbent particles, the apparatus described in the aforementioned patent application on page 19 and in FIG. 8 being modified to the effect that the glass frit (40) is not used, and the plunger (39) consists of the same polymer material as the cylinder (37) and now comprises 21 bores of equal size distributed homogeneously over the entire contact area. The procedure and evaluation of the measurement remain unchanged from EP 0 640 330 A1. The flow is detected automatically.

The permeability (SFC) is calculated as follows:

$$SFC[cm^3s/g]=(Fg(t=0) \times L0)/(d \times A \times WP)$$

where $Fg(t=0)$ is the flow of NaCl solution in g/s, which is obtained using linear regression analysis of the $Fg(t)$ data of the flow determinations by extrapolation to $t=0$, $L0$ is the thickness of the gel layer in cm, d is the density of the NaCl solution in g/cm³, A is the area of the gel layer in cm², and WP is the hydrostatic pressure over the gel layer in dyn/cm².

Permeability (GBP, "Gel Bed Permeability")

The gel bed permeability is measured by the method in published patent application No. US 2005/0 256 757 A1.

EXAMPLES

The base polymer used in the examples which follow was prepared by polymerizing an aqueous monomer solution that comprised sodium acrylate and acrylic acid (corresponding to a neutralization level of the acrylic acid 71 mol %) in a concentration of 41% by weight (sodium acrylate plus acrylic acid based on the total amount), and also 0.75% by weight (based on unneutralized acrylic acid) of polyethylene glycol-4000 (polyethylene glycol having an average molar mass of 4000 g/mol) and 0.46% by weight (based on unneutralized acrylic acid) of triacrylate of triethoxylated glycerol. The initiator system used (based in each case on unneutralized acrylic acid) was 0.184% by weight of sodium persulfate, 0.0007% by weight of hydrogen peroxide and 0.0026% by weight of ascorbic acid. Polymerization was effected in a kneader. For better drying, the gel obtained was extruded and then dried and ground, and the sieve cut from 150 to 710 μm was obtained therefrom. The base polymer thus prepared had a CRC of 36.5 g/g and an AUL 0.3 psi of 14.6 g/g, and comprised 13.0% by weight of extractables. The particle size distribution obtained by means of sieve analysis was:

| | |
|---|---|
| >850 μm | <0.1% by weight |
| 600-850 μm | 10.6% by weight |
| 300-600 μm | 70.8% by weight |
| 100-300 μm | 18.0% by weight |
| <100 μm | <0.5% by weight |

Base polymers of this kind are standard and also commercially available, for example from BASF SE, Ludwigshafen, Germany.

The mixer used in the examples was a Pflugschar® 5R-MK plowshare mixer with capacity 5 L, model VT 5R-MK, with a heating jacket from Gebr. Lödige Maschinenbau GmbH; Elsener Strasse 7-9, 33102 Paderborn, Germany. To measure the temperature of the product in the mixer, a thermocouple was introduced into the opening provided for the purpose in the mixer to such an extent that its tip was at a distance from the heated inner wall of the mixer and was within the product, but could not be impacted by the mixing tools. For additional aluminum hydroxide in examples 1-6, an identical mixer but without heating jacket and thermocouple was used.

The x-ray-amorphous aluminum hydroxide used in the examples was aluminum hydroxide dried gel, catalog no. 511066100, batch number 3048632 from Dr. Paul Lohmann GmbH KG, Hauptstrasse 2, 31860 Emmerthal, Germany. By scanning electron microscope, the powder is found to be in the form of spherical particles having diameters in the region of 20-25 μm, but also some smaller spheres in the region of 5-10 μm. By x-ray diffractogram (measured with a D8 Advance Serie 2 diffractometer from Bruker Corporation, 40 Manning Road, Billerica, MA 01821, U.S.A., with multiple sample changer, Cu anode, divergence slit 0.1° with ASS and Lynx-Eye, 3° aperture), no diffraction mines were measured, which indicates a size of the primary crystallites of distinctly smaller than 2 nm.

The crystalline aluminum hydroxide using the comparative examples was Emplura® hydrargillite, catalog no. 1010911000 from Merck KGaA, Frankfurter Strasse 250, 64293 Darmstadt. By scanning electron microscope, the powder is found to be in the form of irregular particles predominantly in platelet form with dimensions in the region of 5-50 μm. By x-ray diffractogram, the diffraction lines expected for hydrargillite were measured, with a size of the primary crystallites of more than 200 nm.

Example 1

1.2 kg of superabsorbent base polymer were initially charged in the mixer. At 23° C. and a shaft speed of 200 revolutions per minute, by means of a nitrogen-driven two-phase spray nozzle, a solution of 0.08% by weight of ethylene glycol diglycidyl ether, 2.5% by weight of propane-1,2-diol and 3% by weight of water, based in each case on the base polymer, was sprayed on. Subsequently, the shaft speed was reduced to 60 revolutions per minute, and the product temperature was increased to 130° C. and then maintained for 30 minutes.

The superabsorbent obtained was removed from the mixer and samples were analyzed. The values are reported in table 1.

Directly thereafter (the product temperature at that point was about 100° C.), the superabsorbent obtained was mixed in a further mixer at a shaft speed of 200 revolutions per minute with 0.5% by weight, based on the superabsorbent, of x-ray-amorphous aluminum hydroxide (mixing time about one minute) and the sieve cut of 150-710 μm was obtained.

The superabsorbent thus obtained was again analyzed; the measurements obtained are reported in table 1.

Example 2

Example 1 was repeated, except that, after the aluminum hydroxide had been mixed in and before the sieving-off, by means of a nitrogen-driven two-phase nozzle, 3.0% by weight, based on the superabsorbent, of water was also sprayed on. The measurements obtained are reported in table 1.

Example 3

Example 2 was repeated, except using 0.35% by weight of x-ray-amorphous aluminum hydroxide. The measurements obtained are reported in table 1.

Example 4

Example 2 was repeated, except using 0.5% by weight of x-ray-amorphous aluminum hydroxide. The measurements obtained are reported in table 1.

Example 5

Example 2 was repeated, except using 0.75% by weight of x-ray-amorphous aluminum hydroxide. The measurements obtained are reported in table 1.

Example 6 (Comparative)

Example 1 was repeated, except using 0.5% by weight of crystalline aluminum hydroxide rather than x-ray-amorphous aluminum hydroxide. The measurements obtained are reported in table 1.

Evaluation

Examples 1 to 6 show that GBP can be increased by applying aluminum hydroxide without significant loss of CRC and AUL. Comparison between examples 1 and 6 shows that, by addition of water after the addition of x-ray-amorphous aluminum hydroxide, a further rise in GBP is possible. Comparison between examples 1 and 4 shows that, by addition of water after the addition of x-ray-amorphous aluminum hydroxide, a further rise in GBP is possible. Examples 2 to 5 show that, under the experimental conditions employed here, there is an optimum at the addition of 0.5% by weight of x-ray-amorphous aluminum hydroxide. These examples also show that the addition of x-ray-amorphous aluminum hydroxide does not have any significant effect on the swelling kinetics of the superabsorbent.

Example 7

1.2 kg of superabsorbent base polymer were initially charged in the mixer. At 23° C. and a shaft speed of 200 revolutions per minute, 0.5% by weight, based on the superabsorbent, of x-ray-amorphous aluminum hydroxide was added and mixed in for 5 minutes. Subsequently, with unchanged speed and temperature, by means of a nitrogen-driven two-phase spray nozzle, a solution of 0.08% by weight of ethylene glycol diglycidyl ether, 2.5% by weight of propane-1,2-diol and 3% by weight of water, based in each case on the base polymer, was sprayed on. Subsequently, the shaft speed was reduced to 60 revolutions per minute, and the product temperature was increased to 130° C. and then maintained for 30 minutes.

The superabsorbent was cooled down to room temperature and the sieve cut of 150-710 µm was obtained. The superabsorbent obtained was analyzed; the measurements obtained are reported in table 1.

Example 8

Example 7 was repeated, except using 0.5% by weight of crystalline aluminum hydroxide rather than x-ray-amorphous aluminum hydroxide. The measurements obtained are reported in table Evaluation Comparison between examples 7 and 8 again shows that x-ray-amorphous aluminum hydroxide can achieve a considerably greater increase in GBP than crystalline aluminum hydroxide Comparison between examples 1 and 7 shows that the addition of aluminum hydroxide prior to the surface postcrosslinking reaction increases GBP to a greater degree than addition thereafter. These examples too show that the addition of x-ray-amorphous aluminum hydroxide does not have any significant effect on the swelling kinetics of the superabsorbent.

Example 9 (Comparative)

The use of freshly precipitated aluminum hydroxide sol—i.e. x-ray-amorphous but non-pulverulent aluminum hydroxide—described in general terms in EP 233 067 A2, WO 2014/167036 A1, WO 2014/167040 A1 and WO 2014/168858 A1 for surface postcrosslinking of superabsorbents was to be reworked. However, difficulties occurred in the preparation of aluminum hydroxide sold by reworking of the methods specified in these documents.

EP 233 067 A2 describes (pages 14-15) the formation of aluminum hydroxide sol from 8 parts by weight of aluminum chloride hexahydrate and 8 parts by weight of sodium aluminate in aqueous solution. On the basis of the molar masses of aluminum chloride hexahydrate of 241 g/mol and of sodium aluminate of 118 g/mol, this weight ratio of 1:1 corresponds to a molar ratio of 1:2. According to the stoichiometry $AlCl_3 + 3\ NaAl(OH)4 \rightarrow 4\ Al(OH)_3 + 3\ NaCl$, however, the formation of aluminum hydroxide sol would require the molar ratio of 1:3. The pH here must thus still be relatively acidic and there must therefore be no $Al(OH)_3$. EP 233 067 A2 also mentions the formation of aluminum hydroxide sol from 32 parts by weight of aluminum chloride hexahydrate and 15.9 parts by weight of sodium hydroxide in aqueous solution. From the molar masses (NaOH: 40 g/mol, the molar ratio of 1:3 required according to the stoichiometry $AlCl_3 + 3\ NaOH \rightarrow Al(OH)_3 + 3\ NaCl$ is calculated, and so aluminum hydroxide could form thereby. According to the teaching of EP 233 067 A2, however, for preparation of the surface postcrosslinker solution, immediately after the mixing of the reactants or directly in the aqueous solutions thereof, polyol is also added, but this is not mentioned specifically in the specific preparation methods. Thus, however, with the use of the necessary reactants in the correct stoichiometry, what is present therein is not an $Al(OH)_3$ sol, but a non-specific Al salt stabilized by chelate formation with the polyol in solution.

The three latter documents comprise identical methods for preparation of a "Neutralized Aluminum Salt C" from 200 g of 20% by weight aqueous aluminum salt solution to which 130 g of 50% by weight aqueous sodium hydroxide solution are added while stirring until a pH of 7 is attained. The resultant white colloidal suspension was apparently homogenized with a Turnax [sic] stirrer (what is meant is presumably an Ultra-Turrax® from IKA®-Werke GmbH & Co. KG, Janke & Kunkel-Str. 10, 79219 Staufen, Germany) and was then apparently used without further purification for surface postcrosslinking. According to this method, sodium hydroxide solution is in a huge overdose. For the 200 g of aluminum sulfate solution used*20% by weight=40 g of $Al_2(SO_4)_3$ with molar mass 342 g/mol, i.e. 117 mmol of $Al_2(SO_4)_3$, according to the stoichiometry $Al_2(SO_4)_3 + 6$ NaOH → $2$ $Al(OH)_3 + 3$ $Na_2SO_4$, a total of 6*117 mmol=0.7 mol of NaOH is required to form a neutral suspension of $Al(OH)_3$. In fact, 130 g of NaOH solution*50% by weight=65 g of NaOH with molar mass 40 g/mol, i.e. 1.63 mmol, were used, more than twice what was stoichiometrically necessary. It is accordingly not possible here to produce an $Al(OH)_3$ sol, but rather sodium aluminate solution, which must be basic. The stated pH of 7 is not reconcilable with the amount of sodium hydroxide stated.

The three latter documents also comprise identical methods for preparation of a "Neutralized Aluminum Salt D" from 120 g of 20% by weight aqueous aluminum salt solution to which 60 g of 20% by weight aqueous sodium aluminate solution are added while stirring until a pH of 6.5 is attained. For the 120 g of aluminum sulfate solution used*20% by weight=24 g of $Al_2(SO_4)_3$ with molar mass 342 g/mol, i.e. 70 mmol of $Al_2(SO_4)_3$, according to the stoichiometry $Al_2(SO_4)_3 + 6$ $NaAl(OH)_4$→$8$ $Al(OH)_3 + 3$ $Na_2SO_4$, a total of 8*70 mmol=0.56 mol of sodium aluminate is required to form a neutral suspension of $Al(OH)_3$. In fact, 60 g of $NaAl(OH)_4$ solution*20% by weight=12 g of $NaAl(OH)_4$ with molar mass 118 g/mol, i.e. 102 mmol, were used, i.e. less than one fifth of what was stoichiometrically necessary. Accordingly, no $Al(OH)_3$ sol is produced here either; instead, essentially aluminum sulfate solution is conserved.

Example 10 (Comparative)

A 450 mL beaker was initially charged with 149.2 g of 26.8% by weight aqueous aluminum sulfate solution (comprising 117 mmol of $Al_2(SO4)_3$) and stirred magnetically with a stirrer bar. The pH and temperature of the contents of the beaker were measured by means of a pH electrode and thermometer. 59.3 g of 50% by weight sodium hydroxide solution (comprising 741 mmol of NaOH) were introduced into a dropping funnel above the beaker. The sodium hydroxide solution was added dropwise to the beaker (1 drop/second). In a highly exothermic reaction, colorless gel product was formed, which at first accumulated on the pH electrode and ultimately solidified completely. The measured pH was 12.3, although the measurement may be distorted owing to product settled on the electrode.

A repetition of the experiment in which the beaker was placed in an ice bath to remove the heat of reaction and the pH electrode was placed into the reaction mixture only after the addition of every 30 drops of sodium hydroxide solution and then cleaned did not give a different result. The pH rose to 5.2, then the contents of the beaker solidified. In a repetition of the latter experiment without an ice bath, the contents of the beaker solidified at pH 4.4.

No suspension that could be applied to superabsorbent by spraying was obtained.

Example 11 (Comparative)

A 200 mL beaker was initially charged with 104 g of water and stirred magnetically. The water was heated to 40° C., then 26 g of sodium aluminate powder (220 mmol) were added. Stirring was continued at 60 to 70° C. in order to obtain a clear 20% by weight solution, which was then left to cool down to room temperature.

A 450 mL beaker was initially charged with 89.55 g of 26.8% by weight aqueous $Al_2(SO_4)_3$ solution (corresponding to 24 g of $Al_2(SO_4)_3$, 70 mmol), and stirred magnetically with a stirrer bar. The pH and temperature of the contents of the beaker were measured by means of a pH electrode and thermometer. The sodium aluminate solution was introduced into a dropping funnel above the beaker and added dropwise to the beaker (1 drop/second). Only after addition of nearly half the sodium aluminate solution (corresponding to the stoichiometry in the preparation of "Neutralized Aluminum Salt D" mentioned in example 9) had a pH of 3.7 been attained. On addition of the remaining sodium aluminate, the reaction mixture solidified at a measured pH of 5.7.

The experiment was repeated, except adding 60 g of a sodium aluminate solution prepared as described all at once to the aluminum sulfate solution. This achieved a pH of 3.7. Thereafter, in portions each of about 2 g, further sodium aluminate solution was added. After the addition of 85 g in total, a pH of 4.3 was attained and the contents of the beaker were solid.

No suspension that could be applied to superabsorbent by spraying was obtained.

Example 12 (Comparative)

A 150 mL beaker was initially charged with 36.83 g of 26.8% by weight aqueous aluminum sulfate solution (comprising 28.9 mmol of $Al_2(SO_4)_3$) and stirred magnetically with a stirrer bar. 12.24 g of 50% by weight sodium hydroxide solution (comprising 153 mmol of NaOH) were introduced into a dropping funnel above the beaker. The sodium hydroxide solution was added dropwise to the beaker (1 drop/second). On completion of the addition of the sodium hydroxide solution, 16.68 g of water were added and the suspension formed was stirred for a further 15 minutes. Finally, isolated lumps were broken up by stirring with an Ultra-Turrax® for one minute. The pH measured subsequently was 6.65.

Example 13 (Comparative)

Example 1 was repeated, except that, rather than the x-ray-amorphous aluminum hydroxide powder used therein, the aluminum hydroxide sol prepared in example 12 was sprayed on. The amount of aluminum hydroxide applied thereby was 0.5% by weight, and amount of water applied thereby, needed to generate a sprayable dispersion, was 5.3% by weight, based on the superabsorbent. The measurements obtained are reported in table 1.

Evaluation

Examples 9, 10 and 11 show that, in the documents mentioned in example 9, aluminum hydroxide sol has not unambiguously been produced and used, if at all. Example 12 shows that greater amounts of water than those specified in example 9 are necessary to obtain a sprayable aluminum hydroxide sol when the reactants are used even close to the theoretical stoichiometry, and for aluminum hydroxide sol also to be able to form reliably at a pH in the neutral range. Example 13 shows, by comparison with the closest examples 1 and 4, that there is no rise in GBP or it is much less marked when aluminum hydroxide sol is added to the superabsorbent rather than dry pulverulent aluminum hydroxide, optionally followed by water.

TABLE 1

| Example | X-ray-amorphous Al(OH)₃ [% by wt.] | Crystalline Al(OH)₃ [% by wt.] | Remoisturization [% by wt.] | CRC [g/g] | AUL0.9psi [g/g] | GBP [g/g] | VAUL τ (0.3 psi) [s] |
|---|---|---|---|---|---|---|---|
| 1 | — | — | — | 29.1 | 23.8 | 17 | 161 |
|   | 0.5 | — | — | 28.2 | 20.7 | 70 | 155 |
| 2 | — | — | — | 30.5 | 23.0 | 17 | n.d. |
|   | 0.2 | — | 3.0 | 28.7 | 20.8 | 78 | 154 |
| 3 | — | — | — | 30.5 | 22.9 | 14 | n.d. |
|   | 0.35 | — | 3.0 | 28.8 | 20.2 | 86 | 154 |
| 4 | — | — | — | 28.6 | 23.2 | 18 | 173 |
|   | 0.5 | — | 3.0 | 27.1 | 20.3 | 94 | 174 |
| 5 | — | — | — | 29.6 | 22.8 | 14 | n.d. |
|   | 0.75 | — | 3.0 | 28.3 | 19.6 | 88 | 165 |
| 6 | — | — | — | 28.9 | 23.5 | 19 | 162 |
| (Comparative) | — | 0.5 | — | 27.9 | 22.4 | 23 | 166 |
| 7 | 0.5 | — | — | 30.5 | 18.2 | 112 | 177 |
| 8 (Comparative) | — | 0.5 | — | 27.8 | 22.8 | 17 | 165 |
| 13 (Comparative) | 0.5 (as dispersion) | — | 5.3 (as dispersion) | 28.8 | 23.2 | 26 | n.d. |

The invention claimed is:

1. A process for producing a superabsorbent, comprising polymerizing an aqueous monomer solution comprising
   a) at least one ethylenically unsaturated monomer which bears an acid group and optionally is at least partly in salt form,
   b) at least one crosslinker,
   c) at least one initiator,
   d) optionally one or more ethylenically unsaturated monomer copolymerizable with the monomer mentioned under a), and
   e) optionally one or more water-soluble polymer;
   drying a resulting polymer,
   optionally grinding the dried polymer and sieving the ground polymer,
   optionally surface postcrosslinking the dried and optionally ground and sieved polymer,
   wherein, after drying, grinding, or sieving, and, if surface postcrosslinking is conducted, during or after the surface postcrosslinking, adding an x-ray-amorphous aluminum hydroxide powder.

2. The process according to claim 1, wherein 0.01% to 2% by weight, based on the amount of polymer prior to the addition, of x-ray-amorphous aluminum hydroxide is added.

3. The process according to claim 2, wherein 0.2% to 1% by weight, based on the amount of polymer prior to the addition, of x-ray-amorphous aluminum hydroxide is added.

4. The process according to claim 1, wherein the dried and optionally ground and sieved polymer is surface postcrosslinked with a postcrosslinker that forms covalent bonds with polar groups at a surface of the superabsorbent particles.

5. The process according to claim 1, wherein, after the addition of x-ray-amorphous aluminum hydroxide powder, 0.1% to 10% by weight, based on the amount of polymer prior to the addition of the x-ray-amorphous aluminum hydroxide powder, of water is added to the superabsorbent.

6. A superabsorbent obtained by the process of claim 1.

7. An article for absorption of fluids, comprising the superabsorbent of claim 6.

8. A process for producing articles for absorption of a fluid comprising adding the superabsorbent of claim 6.

* * * * *